US012678464B2

(12) United States Patent
Lamb et al.

(10) Patent No.: US 12,678,464 B2
(45) Date of Patent: Jul. 14, 2026

(54) METHODS FOR STEM CELL TRANSPLANTATION

(71) Applicant: The UAB Research Foundation, Birmingham, AL (US)

(72) Inventors: Lawrence S Lamb, Birmingham, AL (US); Shin Mineishi, Vestavia Hills, AL (US); Ayman Saad, Hoover, AL (US)

(73) Assignee: THE UAB RESEARCH FOUNDATION, Birmingham, AL (US)

( * ) Notice: Subject to any disclaimer, the term of this patent is extended or adjusted under 35 U.S.C. 154(b) by 728 days.

(21) Appl. No.: 17/691,477

(22) Filed: Mar. 10, 2022

(65) Prior Publication Data

US 2022/0265720 A1     Aug. 25, 2022

Related U.S. Application Data

(63) Continuation of application No. 15/754,973, filed as application No. PCT/US2016/048738 on Aug. 25, 2016, now abandoned.

(60) Provisional application No. 62/209,721, filed on Aug. 25, 2015.

(51) Int. Cl.

| | |
|---|---|
| A61K 35/28 | (2015.01) |
| A61K 31/436 | (2006.01) |
| A61K 31/5377 | (2006.01) |
| A61K 31/675 | (2006.01) |
| A61K 35/14 | (2015.01) |
| A61K 38/19 | (2006.01) |
| A61K 40/11 | (2025.01) |
| A61K 40/22 | (2025.01) |
| A61K 40/41 | (2025.01) |
| A61P 37/06 | (2006.01) |
| C12N 5/00 | (2006.01) |
| C12N 5/0783 | (2010.01) |
| A61K 45/06 | (2006.01) |

(52) U.S. Cl.
CPC ............ *A61K 35/28* (2013.01); *A61K 31/436* (2013.01); *A61K 31/5377* (2013.01); *A61K 31/675* (2013.01); *A61K 35/14* (2013.01); *A61K 38/193* (2013.01); *A61K 40/11* (2025.01); *A61K 40/22* (2025.01); *A61K 40/418* (2025.01); *A61P 37/06* (2018.01); *C12N 5/0087* (2013.01); *C12N 5/0636* (2013.01); *A61K 45/06* (2013.01); *A61K 2239/38* (2023.05)

(58) Field of Classification Search
None
See application file for complete search history.

(56) References Cited

U.S. PATENT DOCUMENTS

| | | | |
|---|---|---|---|
| 9,907,820 | B2 | 3/2018 | Cooper |
| 2001/0051151 | A1 | 12/2001 | Lamb |
| 2005/0118142 | A1 | 6/2005 | Ildstad |
| 2011/0044959 | A1 | 2/2011 | Trivedi et al. |
| 2012/0269774 | A1 | 10/2012 | Ichim et al. |
| 2013/0216509 | A1 | 8/2013 | Campana et al. |
| 2014/0308250 | A1 | 10/2014 | Handgretinger et al. |
| 2014/0328804 | A1 | 11/2014 | Mcfadden et al. |
| 2016/0175358 | A1 | 6/2016 | Jakobovits et al. |
| 2022/0265720 | A1 | 8/2022 | Lamb et al. |

FOREIGN PATENT DOCUMENTS

| | | |
|---|---|---|
| CN | 103635573 A | 3/2014 |
| CN | 103834615 A | 6/2014 |
| JP | H08511937 A | 12/1996 |
| JP | 2002-535002 A | 10/2002 |
| JP | 2009-517354 | 4/2009 |
| JP | 2013-531043 | 8/2013 |
| JP | 2015-502355 | 1/2015 |
| JP | 7105188 B2 | 7/2022 |
| WO | 2000/044893 A1 | 8/2000 |
| WO | 2007059997 | 5/2007 |
| WO | 2011053750 | 5/2011 |
| WO | 2012009611 | 1/2012 |
| WO | 2012156958 | 11/2012 |
| WO | 2013082366 | 6/2016 |

OTHER PUBLICATIONS

Ashley et al. Best Practice&Reaseach Clinical Haematology 2011, 24, 359-368.*
Luznik, L. et al. "HLA-Haploidentical Bone Marrow Transplantation for Hematologic Malignancies Using Nonmyeloablative Conditioning and High-Dose, Posttransplantation Cyclophosphamide", Biology of Blood and Marrow Transplantation, Jun. 2008.
Baumeister, S.H.C. et al. "Key Aspects of the Immunobiology of Haploidentical Hematopoietic Cell Transplantation" Frontiers in Immunology, Feb. 2020, vol. 11, Article ID 191.
Jamy, O. et al. "Impact of access to care on 1-year mortality following allogeneic blood or marrow transplantation" Bone Marrow Transplantation, Jun. 2021.
Barrett, J.A. et al. "Relapse after allogeneic stem cell transplantation" NIH-PA Author Manuscript, Aug. 2010.
Rochlin, K. "IN8BIO Completes Dosing of First Cohort in Phase 1 Clinical Trial with Allogeneic Gamma Delta T-Cell Therapy in Leukemia Patients Undergoing Hematopoietic Stem Cell Transplant" Aug. 11, 2021.

(Continued)

*Primary Examiner* — Michail A Belyavskyi
(74) *Attorney, Agent, or Firm* — Nicholas J. Landau; Maynard Nexsen PC

(57) ABSTRACT

The present disclosure provides methods of hematopoietic stem cell transplantation (HSCT). In particular, the present disclosure provides a method of HSCT using a combination of an in-vivo T-cell depletion method, with an ex-vivo method of γδ T cell expansion and as T cell depletion. The in-vivo T-cell depletion method depletes (in-vivo) the alloreactive T cells that would otherwise increase the risk of GvHD.

16 Claims, 3 Drawing Sheets

(56)　　　　　References Cited

OTHER PUBLICATIONS

Vodanovic-Jankovic, S. et al. "γδ T Cells Do Not Require Fully Functional Cytotoxic Pathways or the Ability to Recognize Recipient Alloantigens to Prevent Graft Rejection", Biology of Blood and Marrow Transplantation, vol. 12, Issue 11, Nov. 2006, pp. 1125-1134.

Japan Patent Application No. 2018-510483 Office Action issued Aug. 4, 2020.

Nakamae, H. et al."HLA Haplo-Identical Peripheral Blood Stem Cell Transplantation Using High-Dose Cyclophosphamide Post-Transplantation for Poor Prognosis or Refractory Acute Leukemia and Myelodysplastic Syndrome: A Prospective Pilot Study at a Single Center", Blood, Nov. 2013; v.122(21), pp. 3404.

Kanda, J. et al."Outcomes of a 1-day nonmyeloablative salvage regimen for patients with primary graft failure after allogeneic hematopoietic cell transplantation" Bone Marrow Transplantation, vol. 47, 2012, pp. 700-705.

Schriber, J. et al."Granulocyte Colony-Stimulating Factor After Allogeneic Bone Marrow Transplantation" Blood, Sep. 1994; vol. 84(5), pp. 1680-1684.

Stinson, T. J. et al. "Economic analysis of a phase III study of G-CSF vs placebo following allogeneic blood stem cell transplantation" Bone Marrow Transplantation, vol. 20, 2000, pp. 663-666.

Lang, P., et al. "Improved immune recovery after transplantation of TCRαβ/CD19-depleted allografts from haploidentical donors in pediatric patients" Bone Marrow Transplantation, vol. 50, Jun. 2015, pp. S6-S10.

Radestad, E. et al. "Alpha/Beta T-Cell Depleted Grafts as an Immunological Booster to Treat Graft Failure after Hematopoietic Stem Cell Transplantation with HLA-Matched Related and Unrelated Donors" Journal of Immunology Research, Jan. 2014, vol. 2014, Article ID 578741.

U.S. National Library of Medicine: "History of Changes for Study: NCT02193880 Safety of Post-transplant Alpha-beta Depleted T-cell Infusion Following Haploidentical Stem Cell Transplant (Haplo SCT) (ABD)" Dec. 2019 Archive History for NCT02193880.

Chaleff, S. et al. "A large-scale method for the selective depletion of αβ T lymphocytes from PBSC for allogeneic transplantation" Cytotherapy, 2007, vol. 9, No. 8, pp. 746-754.

Schumm, M. et al. "Depletion of T-cell receptor alpha/beta and CD19 positive cells from apheresis products with the CliniMACS device" Cytotherapy, Oct. 2013, vol. 15, No. 10, pp. 1253-1258.

Airoldi, I. et al, "γδ T-cell reconstitution after HLA-haploidentical hematopoietic transplantation depleted of TCR-αβ+/CD19+ lymphocytes" Blood, Apr. 2015, vol. 125, No. 15, pp. 2349-2358.

Li Pira, G. et al. "Selective Depletion of αβ T Cells and B Cells for Human Leukocyte Antigen-Haploidentical Hematopoietic Stem Cell Transplantation. A Three-Year Follow-Up of Procedure Efficiency" Biology of Blood and Marrow Transplantation, Nov. 2016, vol. 22, No. 11, pp. 2056-2064.

Written Opinion of the International Searching Authority, PCT/US2016/048738, Oct. 13, 2016.

Hoppe RT et al., "Hodgkin lymphoma". Journal of the National Comprehensive Cancer Network: JNCCN, Sep. 2011, pp. 1020-1058, vol. 9, Issue 9.

Zelenetz AD et al., "National Comprehensive Cancer N NonHodgkin's lymphomas, version 1.2013", Journal of the National Comprehensive Cancer Network: JNCCN, Mar. 2013, pp. 257-272, vol. 11, Issue 3.

O'Donnell MR et al., "Acute myeloid leukemia, version 2.2013", Journal of the National Comprehensive Cancer Network JNCCN, Sep. 2013, pp. 1047-1055, vol. 11, Issue 9.

O'Brien S et al., "Chronic Myelogenous Leukemia, Version 1.2014" Journal of the National Comprehensive Cancer Network: JNCCN, Nov. 2013, pp. 1327-1340, vol. 11, Issue 11.

Greenberg PL et al., "Myelodysplastic syndromes: clinical practice guidelines in oncology". Journal of the National Comprehensive Cancer Network: JNCCN Jul. 2013, pp. 838-874, vol. 11. Issue 7.

Smetak et al., "Clinical-scale single-step CD4+ and CD8+ cell depletion for donor innate lymphocyte infusion (DILI)", Bone Marrow Transplantation, 2008, pp. 643-650, vol. 41.

Gale RP et al., "Graft-versus-leukemia in bone marrow transplantation. The Advisory Committee of the International Bone Marrow Transplant Registry". Bone marrow transplantation, Jul. 1, 1990, pp. 94-97, vol. 6, Issue 1. (Abstract Only).

Ferrara JL et al., "Acute graft versus host disease: pathophysiology, risk factors, and prevention strategies", Clinical advances in hematology & oncology: H&O, May 2005, pp. 415-419, vol. 3, Issue 5. (Abstract Only).

Lamb LS, Jr. et al., "Increased frequency of TCR gamma delta+ T cells in disease-free survivors following T celldepleted, partially mismatched, related donor bone marrow transplantation for leukemia", Journal of Hematotherapy, Oct. 1996, pp. 503-509. vol. 5, Issue 5. (Abstract Only).

Lamb LS, Jr. et al., "Influence of T cell depletion method on circulating gammadelta T cell reconstitution and potential role in the graft-versus-leukemia effect", Cytotherapy, 1999, pp. 7-19, vol. 1, Issue 1. (Abstract Only).

Boismenu R et al., "An innate view of gamma delta T cells", Curr Opin Immunol, Feb. 1997, pp. 57-63, vol. 9, Issue 1. (Abstract Only).

Ellison CA et al., "Gamma delta T cells in the pathobiology of murine acute graft-versus-host disease. Evidence that gamma delta T cells mediate natural killer-like cytotoxicity in the host and that elimination of these cells from donors significantly reduces mortality", J Immunol, Nov. 1, 1995, pp. 4189-4198, vol. 155, Issue 9. (Abstract Only).

Schilbach KE et al., "Human gammadelta T lymphocytes exert natural and IL-2-induced cytotoxicity to neuroblastoma cells". J Immunother, Oct. 2000, pp. 536-548, vol. 23, Issue 5. (Abstract Only).

Cela Me et al., "Gamma delta T lymphocyte regeneration after T lymphocyte-depleted bone marrow transplantation from mismatched family members or matched unrelated donors". Bone Marrow Transplant, Feb. 1996, pp. 243-247, vol. 17, Issue 2. (Abstract Only).

Yabe M et al., "Transition of Tcell receptor gamma/delta expressing double negative (CD4-/CD8-) lymphocytes after allogeneic bone marrow transplantation", Bone Marrow Transplant, Nov. 1994, pp. 741-746, vol. 14, Issue 5. (Abstract Only).

Viale M et al., "TCR gamma/delta positive lymphocytes after allogeneic bone marrow transplantation", Bone Marrow Transplant, Sep. 1992, pp. 249-253, vol. 10, Issue 3. (Abstract Only).

Tsuji S et al., "Gamma delta T cells are secondary participants in acute graft-versus-host reactions initiated by CD4+ alpha beta T cells", European Journal of Immunology, Feb. 1996, pp. 420-427, vol. 26, Issue 2. (Abstract Only).

Mayumi H et al., "Cyclophosphamide-induced immunological tolerance: an overview". Immunobiology, Jul. 1996, pp. 129-139, vol. 195 Issue 2. (Abstract Only).

Henslee PJ et al., "T cell depletion of HLA and haploidentical marrow reduces graft-versus-host disease but it may impair a graft-versus leukemia effect." Transplantation Proceedings 1987, 19:2701-6.

"Graft vs. Host Disease" Cleveland Clinic, pp. 1-15, available at https://my.clevelandclinic.org/health/diseases/10255-graft-vs-host-disease-an-overview-in-bone-marrow-transplant, last visited Dec. 6, 2024.

Hutt Daphna "Engraftment, Graft Failure, and Rejection" Chap. in Kenyon M and Babic A "The European Blood and Marrow Transplantation Textbook for Nurses", Nov. 22, 2017, 12 pages available at https://www.ncbi.nlm.nih.gov/books/NBK543659/.

Ciceri Fabio et al., "Haploidentical HSCT" Chap. on Carreras at al. "The EBMT Handbook: Hematopoietic Stem Cell Transplantation and Cellular Therapies" 7th ed. Springer; 2019, available at https://www.ncbi.nlm.nih.gov/books/NBK553970/?report=printable.

Lamb LS, Jr. et al., "Increased Frequency of TCR+ T Cells in Disease-Free Survivors Following T Cell-Depleted, partially Mismatched, Related Donor Bone Marrow Transplantation for Leukemia" Journal of Hematotherapy, 5:503-509 (1996).

(56)     References Cited

OTHER PUBLICATIONS

Muranski Pawel, et al., "Increased intensity lymphodepletion and adoptive immunotherapy-how far can we go?" Nature Clinical Practice Oncology, Dec. 2006, vol. 3, No. 12.

Kawanishi et al., "Effect of T cell subset dose on outcome of T cell-depleted bone marrow transplantation", Bone Marrow Transplantation, 1997, pp. 1069-1077, vol. 19.

Office Action received for European Patent Application No. 16840139.6, mailed on Mar. 12, 2020, 05 pages.

Examination Report received for Australian Patent Application No. 2016312610, mailed on Apr. 14, 2022, 03 pages.

Office Action received for Canadian Patent Application No. 2996522, mailed on Sep. 27, 2022, 05 pages.

Search Report received for Chinese Patent Application No. 201680053465.0, mailed on Dec. 11, 2020, 02 Pages.

Extended European Search Report received for European Patent Application No. 16840139.6, mailed on Feb. 4, 2019, 09 pages.

Examination Report received for Israel Patent Application No. 257678, mailed on Nov. 8, 2020, 03 pages.

Examination Report received for Israel Patent Application No. 257678, mailed on May 10, 2022, 03 pages.

Gomes et al., "Targeting γδ T lymphocytes for cancer immunotherapy: from novel mechanistic insight to clinical application", Cancer research, Dec. 15, 2010, pp. 10024-10027, vol. 70, Issue 24.

Office Action received for Japanese Patent Application No. 2018-510483, mailed on Jun. 15, 2021, 8 pages including English translation.

Office Action received for European Patent Application No. 16840139.6, mailed on Mar. 10, 2021, 05 pages.

Office Action received for Japanese Patent Application No. 2022-110221, mailed on Aug. 8, 2023, 6 pages including English translation.

International Preliminary Report on Patentability received for International Patent Application No. PCT/US2016/048738, mailed on Mar. 8, 2018, 6 pages.

Perko et al., "Gamma Delta T Cell Reconstitution Is Associated with Fewer Infections and Improved Event-Free Survival after Hematopoietic Stem Cell Transplantation for Pediatric Leukemia", Biol Blood Marrow Transplant, Jan. 2015, pp. 130-136, vol. 21, Issue 1.

First Office Action received for Chinese Patent Application No. 201680053465.0, mailed on Dec. 21, 2020, 08 pages.

Second Office Action received for Chinese Patent Application No. 201680053465.0, mailed on Sep. 3, 2021, 08 pages.

Office Action received for European Patent Application No. 16840139.6, mailed on Apr. 28, 2022, 04 pages.

Tefferi A et al., "Primary myelofibrosis: 2013 update on diagnosis, risk-stratification, and management". American journal of hematology, 2013, pp. 141-150, vol. 88.

Copelan EA, "Hematopoietic stem-cell transplantation". The New England journal of medicine, Apr. 27, 2006, pp. 1813-1826, vol. 354.

Lee SJ et al., "High-resolution donor-recipient HLA matching contributes to the success of unrelated donor marrow transplantation", Blood, Dec. 15, 2007, pp. 4576-4583, vol. 110, Issue 13.

Alshemmari S et al., "Haploidentical hematopoietic stem-cell transplantation in adults", Bone marrow research, 2011, 11 Pages, vol. 2011.

Aversa F et al., "Full haplotype-mismatched hematopoietic stem-cell transplantation: a phase II study in patients with acute leukemia at high risk of relapse". Journal of clinical oncology: official journal of the American Society of Clinical Oncology, May 20, 2005, pp. 3447-3454, vol. 23, Issue 15.

Horowitz MM, et al., "Graft-versus-leukemia reactions after bone marrow transplantation", Blood, Feb. 1, 1990, pp. 555-562, vol. 75, Issue 3.

Oevermann L et al., "New strategies for haploidentical transplantation", Pediatric research Apr. 2012, pp. 418-426, vol. 71, Issue 4.

Lamb LS, Jr. et al., "gammadelta T cells: a new frontier for immunotherapy? Biology of blood and marrow transplantation", Journal of the American Society for Blood and Marrow Transplantation, 2005, pp. 161-168, vol. 11.

Moretta L et al., "Killer lg-like receptor-mediated control of natural killer cell alloreactivity in haploidentical hematopoietic stem cell transplantation". Blood, Jan. 20, 2011, pp. 764-771, vol. 117, Issue 3.

Palmer JM et al., "Clinical relevance of natural killer cells following hematopoietic stem cell transplantation". Journal of Cancer, 2013, pp. 25-35, vol. 4.

Gadder KT et al., "Long term disease-free survival in acute leukemia patients recovering with increased gammadelta T cells after partially mismatched related donor bone marrow transplantation", Bone Marrow Transplant, 2007, pp. 751-157, vol. 39.

Handgretinger R et al., "New approaches to graft engineering for haploidentical bone marrow transplantation", Seminars in oncology, Dec. 2012, pp. 664-673, vol. 39, Issue 6.

Girardi M et al., "Regulation of cutaneous malignancy by gammadelta T cells", Science Oct. 19, 2001, pp. 605-609, vol. 294.

Kaminski MJ et al.,"Killing of skin-derived tumor cells by mouse dendritic epidermal T-cells". Cancer Research, Sep. 1, 1993, pp. 4014-4019, vol. 53.

Groh V et al., "Broad tumor-associated expression and recognition by tumor-derived gamma delta T cells of MICA and MICB", Proceedings of the National Academy of Sciences of the United States of America, Jun. 1999, pp. 6879-6884, vol. 96.

Bauer S et al., "Activation ofNK cells and T cells by NKG2D, a receptor for stress-inducible MICA", Science Jul. 30, 1999, pp. 727-729, vol. 285.

Groh V et al., "Recognition of stress-induced MHC molecules by intestinal epithelial gammadelta T cells". Science, Mar. 13, 1998, pp. 1737-1740, vol. 279.

Blazar BR et al., "Murine gamma/delta-expressing T cells affect alloengraftment via the recognition of nonclassical major histocompatibility complex class lb antigens". Blood, May 15, 1996, pp. 4463-4472, vol. 87, Issue 10.

Drobyski WR et al., "Donor gamma delta T lymphocytes promote allogeneic engraftment across the major histocompatibility barrier in mice", Blood, Feb. 1, 1997, pp. 1100-1109, vol. 89, Issue 3.

Drobyski WR et al., "Tcell depletion plus salvage immunotherapy with donor leukocyte infusions as a strategy to treat chronic-phase chronic myelogenous leukemia patients undergoing HLA-identical sibling marrow transplantation. [erratum appears in Blood Feb. 15, 2000;95(4):113]", Blood, Jul. 15, 1999, pp. 434-441, vol. 94, Issue 2.

Neipp M et al., "T-cell depletion of allogeneic bone marrow using anti-alphabetaTCR monoclonal antibody: prevention of graftversus-host disease without affecting engraftment potential in rats". Exp Hematol, 1999, pp. 860-867, vol. 27.

Lamb LS, Jr et al., "Human gammadelta( +) T lymphocytes have in vitro graft vs leukemia activity in the absence of an allogeneic response". Bone Marrow Transplant 2001, pp. 601-606, vol. 27.

Keever-Taylor CA et al., "Effect of I-ILA disparity, ABO incompatibility, and method of Tcell depletion", Biology of Blood & Marrow Transplantation, 2001, pp. 620-630, vol. 7.

Mehta J et al., "Bone marrow transplantation from partially HLA-mismatched family donors for acute leukemia: single-center experience of 201 patients". Bone Marrow Transplant, 2004, pp. 389 96, vol. 33.

Lamb LS HLMP, et al., "Influence of T cell depletion method on circulating gd+ T cell reconstitution and potential role in the graft-versus-leukemia effect". Cytotherapy 1999, pp. 7-19, vol. 1 Issue 1.

Eto M et al., "Specific destruction of host-reactive mature T cells of donor origin prevents graft-versus-host disease in cyclophosphamide-induced tolerant mice". Journal of immunology 1991, pp. 1402-1409, vol. 146, Issue 5.

Strauss G et al., "Induction of apoptosis and modulation of activation and effector function in T cells by immunosuppressive drugs", Clinical and experimental immunology, 2002, pp. 255-266, vol. 128.

Luznik L et al., "Posttransplantation cyclophosphamide facilitates engraftment of major histocompatibility complex-identical allogeneic marrow in mice conditioned with low dose total body irradiation",

(56)                    References Cited

OTHER PUBLICATIONS

Biology of blood and marrow transplantation: journal of the American Society for Blood and Marrow Transplantation, 2002, pp. 131-138, vol. 8.

Luznik L, et al., "Durable engraftment of major histocompatibility complex-incompatible cells after nonmyeloablative conditioning with fludarabine, low-dose total body irradiation, and posttransplantation cyclophosphamide". Blood, Dec. 1, 2001, pp. 3456-3464, vol. 98. Issue 12.

Burroughs LM et al., "Comparison of outcomes ofHLA-matched related, unrelated, or HLA-haploidentical related hematopoietic cell transplantation following non-myeloablative conditioning for relapsed or refractory Hodgkin lymphoma". Biology of blood and marrow transplantation : journal of the American Society for Blood and Marrow Transplantation 2008, pp. 1279-1287, vol. 14.

Luznik L et al., "HLA-haploidentical bone marrow transplantation for hematologic malignancies using nonmyeloablative conditioning and high-dose, posttransplantation cyclophosphamide". Biology of blood and marrow transplantation : journal of the American Society for Blood and Marrow Transplantation 2008, pp. 641-650, vol. 14.

Bronstein CG et al., "Alternative donor transplantation after reduced intensity conditioning: results of parallel phase 2 trials using partially HLA-mismatched related bone marrow or unrelated double umbilical cord blood grafts". Blood, Jul. 14, 2011, pp. 282-288, vol. 118, Issue 2.

Alvamas JC et al., "National Comprehensive Cancer N: Acute lymphoblastic leukemia. Journal of the National Comprehensive Cancer Network", JNCCN, Jul. 2012, pp. 858-914, vol. 10, Issue 7.

Office action received for Canadian Patent Application No. 2996522, mailed on Sep. 23, 2024, 04 pages.

Extended European Search Report received for European Patent Application No. 24156525.8, mailed on Dec. 20, 2024, 12 pages.

Notice of Reasons for Refusal received for Japanese Patent Application No. 2022-110221, mailed on Jun. 4, 2024, 11 pages including English translation.

Request for the Submission of an Opinion received for Korean Patent Application No. 10-2018-7008284, mailed on Apr. 26, 2024, 07 pages including English translation.

Final Rejection received for Korean Patent Application No. 10-2018-7008284, mailed on Oct. 30, 2024, 2 pages including English translation.

* cited by examiner

METHODS FOR STEM CELL TRANSPLANTATION

CROSS-REFERENCE TO RELATED APPLICATIONS

This application is a "continuation" under 35 U.S.C. § 120 of U.S. patent application Ser. No. 15/754,973, filed on 23 Feb. 2018 (abandoned); which is a national stage under 35 U.S.C. § 371 of International Pat. App. PCT/US16/48738, filed 25 Aug. 2016 (abandoned); which cites for priority under 35 U.S.C. § 119 to provisional U.S. Pat. App. No. 62/209,721, filed 25 Aug. 2015 (abandoned). All of the foregoing patent applications are incorporated herein by reference in their entireties.

STATEMENT REGARDING FEDERALLY SPONSORED RESEARCH OR DEVELOPMENT

This invention was made with government support under grant number CA076667 awarded by the National Institutes of Health. The government has certain rights in the invention.

In this context "government" refers to the government of the United States of America.

BACKGROUND

Allogeneic hematopoictic stem cell transplantation (allo HSCT) is a potentially curative treatment for many patients with hematological malignancies.[1] The clinically preferred source for stem cells is a human leukocyte antigen (HLA) matched sibling donor or an HLA-matched unrelated donor.[2] Unfortunately many patients, particularly those of ethnic minority groups, do not have an HLA-matched sibling or unrelated donor. Registry searches can also be inappropriately time-consuming in some high-risk patients. Therefore, alternative sources of HSCT grafts have been clinically used. These options include the use of donor cells from a partially HLA matched (haploidentical) family member.[3] Haploidentical HSCT has been shown to achieve long-term survival and cure in patients who require allogeneic HSCT with no HLA-matched donor.[3] However, the success of haploidentical HSCT has been hindered by multiple complications. The HLA disparity between the donor and recipient can induce high risks of graft rejection, graft versus host discase (GvHD), and delayed immune reconstitution with subsequent infectious complications.[4] The use of intense immunosuppression regimens (to prevent GvHD) may, at least in theory, abrogate the graft versus tumor (GvT) effect portending an increased risk of disease relapse. The GvT effect after allo HSCT has been shown to correlate with a decreased risk of relapse.[5,6] Thus, the infused donor T-cells can have beneficial effects (engraftment, immune reconstitution, and GvT) and also exert a harmful (and sometimes fatal) effect of GvHD. For these reasons, researchers have looked at ways to engineer cellular therapies that will provide the optimum ratio of T-cell subsets that may provide a sufficient number of cells to maintain engraftment and optimize GvT effect, while minimizing the allo-reactive T-cells that can lead to GvHD.

The present disclosure provides methods and compositions useful in HSCT that maximize a beneficial effect of infused donor T-cells (including, but not limited to, engraftment, immune reconstitution, and GvT) while minimizing a harmful effect (such as, but not limited to, GvHD).

SUMMARY OF THE INVENTION

The present disclosure provides a method of HSCT using a combination of an in-vivo T-cell depletion method after transplantation of minimally manipulated peripheral blood stem cells (PBSC), with an ex-vivo method of γδ T cell enrichment and/or expansion and/or as T cell depletion to provide improved methods of HSCT.

In a first aspect, the method of HSCT comprises: i) administering to a subject on day 0 a haploidentical hematopoietic stem cell graft infusion comprising PBSC; ii) administering to the subject an agent which provides in vivo T cell depletion; iii) optionally expanding a population of γδ T cells ex vivo; and iv) administering to the subject a second graft infusion comprising T cells enriched in γδ T cells and depleted in αβ T cells.

In a second aspect, the method of HSCT comprises: i) administering to a subject on day 0 a minimally manipulated haploidentical hematopoietic stem cell graft infusion comprising PBSC; ii) administering to the subject an agent which provides in vivo T cell depletion; iii) optionally expanding a population of γδ T cells ex vivo; and iv) administering to the subject a second graft infusion comprising T cells enriched in γδ T cells and depleted in αβ T cells.

In a third aspect, the method of HSCT comprises: i) administering to a subject on day 0 a haploidentical hematopoictic stem cell graft infusion comprising PBSC; ii) administering to the subject an agent which provides in vivo T cell depletion; iii) expanding a population of γδ T cells ex vivo; iv) administering to the subject a second graft infusion comprising the expanded population of γδ T cells, wherein the expanded population of γδ T cells is enriched in γδ T cells and depleted in αβ T cells.

In a fourth aspect, the method of HSCT comprises: i) administering to a subject on day 0 a minimally manipulated haploidentical hematopoietic stem cell graft infusion comprising PBSC; ii) administering to the subject an agent which provides in vivo T cell depletion; iii) expanding a population of γδ T cells ex vivo; iv) administering to the subject a second graft infusion comprising the expanded population of γδ T cells, wherein the expanded population of γδ T cells is enriched in γδ T cells and depleted in αβ T cells.

In a fifth aspect, the method of HSCT comprises: i) obtaining a pool of PBSC from a haploidentical donor; ii) splitting the pool of PBSC into a first portion of PBSC to provide a PBSC product and a second portion of PBSC that is manipulated to provide a γδ T cell product which is enriched in γδ T cells and depleted in αβ T cells; iii) administering to a subject on day 0 a hematopoietic stem cell graft infusion comprising the PBSC product; iv) administering to the subject an agent which provides in vivo T cell depletion; v) optionally expanding a population of γδ T cells ex vivo in the γδ T cell product and vi) administering to the subject a second graft infusion comprising the γδ T cell product.

In a sixth aspect, the method of HSCT comprises: i) obtaining a pool of PBSC from a haploidentical donor; ii) splitting the pool of PBSC into a first portion of PBSC which is minimally manipulated to provide a PBSC product and a second portion of PBSC that is manipulated to provide a γδ T cell product which is enriched in γδ T cells and depleted in αβ T cells; iii) administering to a subject on day 0 a hematopoietic stem cell graft infusion comprising the PBSC product; iv) administering to the subject an agent which provides in vivo T cell depletion; v) optionally expanding a population of γδ T cells ex vivo in the γδ T cell product and vi) administering to the subject a second graft infusion comprising the γδ T cell product.

In a seventh aspect, the method of HSCT comprises: i) obtaining a pool of PBSC from a haploidentical donor; ii) splitting the pool of PBSC into a first portion of PBSC to provide a PBSC product and a second portion of PBSC that is manipulated to provide a γδ T cell product which is enriched in γδ T cells and depleted in αβ T cells; iii) administering to a subject on day 0 a hematopoietic stem cell graft infusion comprising the PBSC product; iv) administering to the subject an agent which provides in vivo T cell depletion; v) expanding a population of γδ T cells ex vivo in the γδ T cell product and vi) administering to the subject a second graft infusion comprising the γδ T cell product.

In an eighth aspect, the method of HSCT comprises: i) obtaining a pool of PBSC from a haploidentical donor; ii) splitting the pool of PBSC into a first portion of PBSC which is minimally manipulated to provide a PBSC product and a second portion of PBSC that is manipulated to provide a γδ T cell product which is enriched in γδ T cells and depleted in αβ T cells; iii) administering to a subject on day 0 a hematopoietic stem cell graft infusion comprising the PBSC product; iv) administering to the subject an agent which provides in vivo T cell depletion; v) expanding a population of γδ T cells ex vivo in the γδ T cell product and vi) administering to the subject a second graft infusion comprising the γδ T cell product.

In certain embodiments of the above aspects, the described methods of HSCT will maximize a beneficial effect of infused donor T-cells (including, but not limited to, engraftment, immune reconstitution, and GvT). In certain embodiments of the above aspects, the described method of HSCT will minimize a harmful effect of infused donor T-cells (such as, but not limited to, GvHD). In certain embodiments of the above aspects, a combination of the foregoing is achieved. In certain embodiments of the above aspects, the PBSC grafts are collected from haploidentical donors and the cell product divided into a minimally manipulated HSCT product that will be administered to the subject on day 0 (as is standard in HSCT) and a γδ T cell product that will be administered to the subject after day 0. In certain embodiment, the γδ T cell product is administered to the subject up to 25 days after day 0. In certain embodiments, γδ T cell product is administered to the subject ≥3 days after in vivo T cell depletion is initiated. In certain embodiments, the γδ T cell product is expanded ex vivo to increase the number of γδ T cells in the γδ T cell product. In certain embodiments, the γδ T cell product is enriched in γδ T cells. In certain embodiments, the γδ T cell product is depleted in αβ T cells. In certain embodiments, the γδ T cell product is expanded ex vivo to increase the number of γδ T cells in the γδ T cell product and depleted in αβ T cells. In certain embodiments, the γδ T cell product is enriched in γδ T cells and depleted in αβ T cells.

In certain embodiments of the above aspects, the methods of the present disclosure may be used in conjunction with any condition for which HSCT is used.

In certain embodiments of the above aspects, the methods of the present disclosure may be used in conjunction with a preparative chemotherapy regimen; such preparative chemotherapy regimen is preferably initiated prior to day 0.

In certain embodiments of the above aspects, the methods of the present disclosure are used in combination with an in vivo T cell depletion protocol which is initiated after day 0. In certain embodiments of the above aspects, the in vivo T cell depletion protocol is post-transplant administration of cyclophosphamide (CY).

In certain embodiments of the above aspects, the methods of the present disclosure may be used in conjunction with a GvHD prophylaxis regimen; such GvHD prophylaxis regimen is preferably initiated after day 0.

In certain embodiments of the above aspects, the methods of the present disclosure may be used in conjunction with growth factor treatment; such growth factor treatment is preferably initiated after day 0.

DETAILED DESCRIPTION

Definitions

Figure 1:
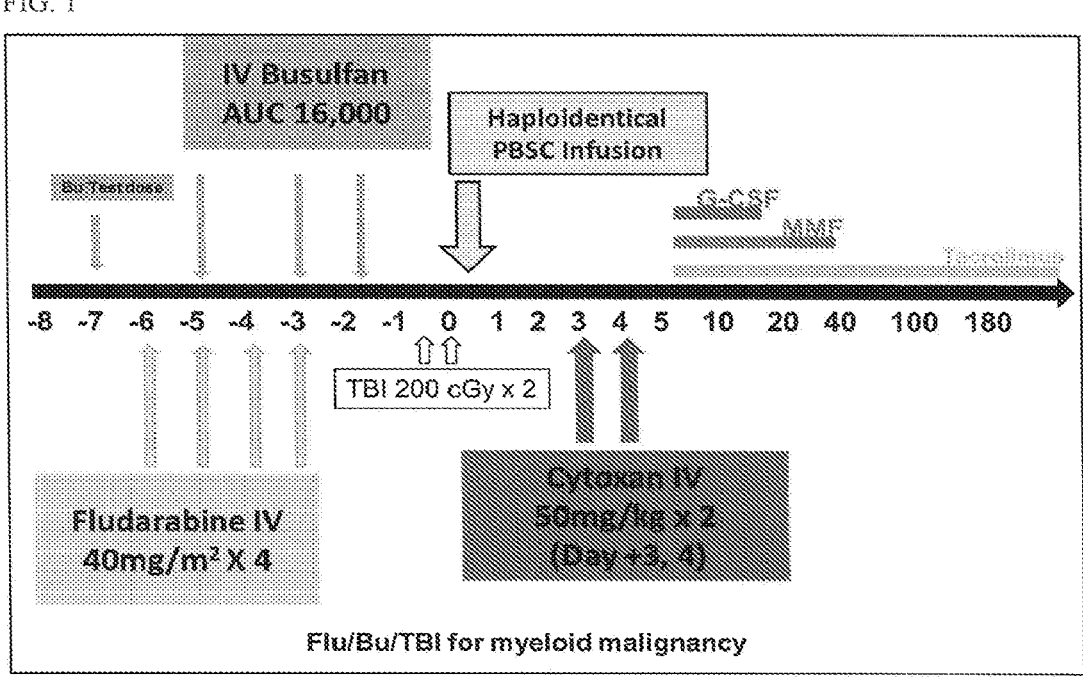
FIG. 1 Shows one embodiment of a preparative regimen for myeloid diseases using Fludarabine/Busulfan/TBI.

As used herein, the term "minimally manipulated" means that the PBSC pool isolated from a donor (such as a haploidentical donor) is not subject methods or procedures that alter the relevant biological characteristics of the cell. The act of removing a portion of the PBSCs from the PBSC pool isolated from a donor (such as to produce a γδ T cell product) as described herein or other routine steps in the preparation, processing and/or storage of the PBSC pool (such as, but not limited to, density-gradient separation, cell selection, centrifugation, and cryopreservation) results in a PBSC pool that is still "minimally manipulated" as the sampling does not enrich and/or deplete a particular population of cells. In a particular aspect, the PBSC pool isolated from a donor (such as a haploidentical donor) is not subject methods or procedures that enrich and/or deplete a particular population of cells (such as, but not limited to, γδ T cells) from the PBSC pool prior to administration to the subject.

As used herein the term "depleted in" means that the number or concentration of a particular cell type in a population of cells has been decreased (for example as the result of a particular manipulation or procedure) from an initial original level to a reduced second level. The term does not require a complete removal of the particular cell type from the population of cells. As an example, a population of T cells is "depleted in" αβ T cells if the number or concentration of αβ T cells in a composition administered to a subject is decreased as compared to the number or concentration of αβ T cells originally present (such as in a pool of PBSCs obtained from a donor).

As used herein the term "enriched in" means that the number or concentration of a particular cell type in a population of cells has been increased (for example as the result of a particular manipulation or procedure) from an initial original level to a higher second level. As an example, a population of T cells is "enriched in" γδ T cells if the number or concentration of γδ T cells in a composition administered to a subject is increased as compared to the number or concentration of γδ T cells originally present (such as in a pool of PBSCs obtained from a donor).

General Description

The majority (~80%) of infused donor lymphocytes are T-cells (other infused cells are B-cells and NK cells). T-cells have been shown to be the key player in the post-transplant immune phenomena (stem cell engraftment, GvHD, GVT, and immune reconstitution) with B-cells and NK cells likely contributing supportive roles (1, 7). The majority (~95%) of T-cells carries alpha-beta T-cell receptors (αβ-TCR); referred to as alpha-beta T-cells (αβ T-cells). A small proportion of T-cells carry a different T-cell receptor, γδ-TCR, referred to as gamma-delta T-cells (γδ T cells) The γδ T cells have been shown to have an anti-tumor activity. They are considered to be a part of the innate immune system preventing development of new cancer and also protecting from infections via immune surveillance function (8). Unlike the common T-cell subtype, αβ T-cells, γδ T cells do not require antigen recognition to kill malignant cells (9). Thus, they have been advocated for use against cancer (9). The NK cells, another type of innate immune cells, have also shown to have an anti-tumor effect and to promote immune reconstitution after HCT without increasing the risk of GvHD (10, 11).

γδ T cells have been shown to have an anti-leukemic effect in partially mismatched transplant without increasing the risk of GvHD (12, 13). In a retrospective analysis, the 5-year leukemia-free survival (LFS) and overall survival (OS) was higher in patients who recovered with increased γδ T cells as compared to those with normal or decreased numbers; 54 vs 19% (P<0.0003) and 71 vs 20% (P<0.0001) respectively. There were no differences in the incidence of GvHD in both groups (P=0.96) (14). Handgretenger et al. used as T-cell depletion to preserve the γδ T cells with haploidentical HCT. These studies showed rapid engraftment with rapid immune reconstitution (8, 15).

Haploidentical transplant patients are currently being gathered into a Phase I trial in which patients receive post-transplant cyclophosphamide (CY) following a minimally manipulated graft. A second graft from the same donor is selectively depleted of αβ T cells and infused on post-HSCT day +7. To this point, three patients have been enrolled on the study without evidence of GvHD.

Unlike αβ T cells which recognize specific processed peptide antigens presented on MHC molecules by antigen presenting cells (APCs), γδ T cells appear to directly recognize and respond to a variety of MHC-like stress-induced self-antigens expressed by malignant cells (12-16). Thus, γδ T cells can recognize malignant cells through less specific mechanisms that require no prior antigen exposure or priming, a function that is shared by other innate immune cells such as macrophages and NK cells (8).

Animal studies and indirect evidence from human allogeneic transplant studies suggest that 76 T cells can facilitate alloengraftment. Blazar (23), in a murine allogeneic transplant model, found that donor γδ T cells facilitate the engraftment of T-cell depleted (TCD) donor bone marrow. When TCD C.B-17"WO" donor marrow was supplemented with up to $3 \times 10^6$ γδ T cells prior to infusion into B6 recipients, donor chimerism increased by approximately 40%. Drobyski noted similar findings in C57BL/6 [H-$2^b$]–B1-.BR [H-$2^k$] mismatched mice (24), and later showed that the γδ T cells dose necessary to facilitate engraftment did not result in lethal murine GvHD (25). Nicpp (26) showed similar findings in a rat model where lethally irradiated (Wistar Furth WF-RTIA) rats were reconstituted with $1 \times 10^8$ αβ TCD bone marrow. All animals engrafted with a mean of 92±4% donor cells and no clinical evidence of GvHD. Studies comparing patients who received αβ TCD grafts with those receiving pan-TCD grafts also show a positive association between the number of clonable γδ T cells in the graft with less time to engraftment (27, 28).

γδ T Cells do not Initiate GvHD

Both murine and human studies suggest that γδ T cells are not primary initiators of GvHD and may in fact modulate the GvHD activity of αβ T cells. Drobyski (25) showed that large doses of IL-2 expanded γδ T cells could be infused into lethally irradiated MHC-disparate mice (C57BL/6 [H-$2^b$] a BIO.BR [H-2k] and C57BL/6 [H-$2^b$] a B6D2F1 [H-$2^{b/d}$]) without causing GvHD. Ellison (29) noted that γδ T cells were activated in the GvHD reaction but found no evidence that GvHD was initiated by γδ T cells. This work is in agreement with later studies by Drobyski (25) who showed that although activated γδ and naïve αβ T cells exacerbated GvHD when infused together, delaying the infusion of αβ T cells by two weeks resulted in improved survival. In human studies, Schilbach (30) and Lamb (31) found γδ T cells not to be substantially activated in the in vitro allogeneic mixed lymphocyte culture. Several post-BMT studies have shown transient increases in γδ T cells (32-34) but have not associated this finding with GvHD, although Tsuji (35) found that γδ T cells could be recruited into lesions and activated by CD4+αβ T cells. Several studies that compare outcomes of patients who received αβ TCD grafts with patients who received pan-TCD grafts all show a lower incidence of GvHD in the as TCD group, suggesting that infusion of γδ T cells in the graft does not subject the patient to an increased risk of GvHD (36, 37). Whether 7s T cells are truly less likely to contribute to the development of GvHD remains untested, however.

Six-year survival data from 25 patients who developed a spontaneous increase in γδ T cells during the first year following BMT for ALL or AML show a significant improvement in disease-free survival (DFS) when compared with similar risk patients (p=0.009 for ALL patients and 0.045 for AML patients) (12, 38). A finding from the study was the persistence of an increased number of Vδ1+γδ T cells in surviving patients, sometimes for several years. The persistence of the cells is dependent on the method of T cell depletion, as patients who received αβ T cell-depleted grafts were more likely to develop and sustain increased γδ T cell numbers than patients who received grafts that were depleted with OKT3, a pan T cell monoclonal antibody (p=0.05) (38).

The administration of CY within a few days after infusion of T-cell replete HCT depletes allo-reactive T-cells of both the donor and host, thus inhibiting both GvHD and graft rejection respectively (17-21). It is hypothesized that high-dose CY can deplete the proliferating allo-reactive T-cells sparing the non-proliferative (inactive) T-cells (21). The use of post-transplant cyclophosphamide after haploidentical HCT has shown promising results by investigators at Johns Hopkins University and Fred Hutchinson Cancer Research Center (22). The most unfortunate outcome of this approach remained the high relapse rate of 51% at 1 year (23). The Bone Marrow Transplant Clinical Trials Network (BMT-CTN) conducted a clinical trial (CTN 0603) using the same approach of haploidentical HCT with a reported relapse rate of 45% (24). Thus despite the reduction of GvHD using this approach in haploidentical HCT, the high risk of relapse (45-51%) remained a challenge. The increased risk of relapse may be due to the lack of effective graft versus tumor effect. It is particularly apparent with the use of non-myeloablative regimens, as graft versus leukemia (GVL) effect is the only anti-tumor effect in this setting.

Methods of HSCT

The present disclosure provides methods of HSCT. In one embodiment, the present disclosure provides a method of HSCT using a combination of an in-vivo T-cell depletion method (for example, post-transplant cyclophosphamide), with an ex-vivo method of γδ T cell expansion and αβ T cell depletion (using, for example the CLINIMACS® System). The in-vivo T-cell depletion (for example, infusion of CY after infusion of a minimally manipulated stem cell graft) depletes (in-vivo) the alloreactive T cells that would otherwise increase the risk of GvHD. The ex-vivo expanded/activated γδ T cell product will be selectively depleted of αβ T cells but will also include a secondary population of NK cells.

In one embodiment, the method of HSCT comprises: i) administering to a subject on day 0 a haploidentical hematopoietic stem cell graft infusion comprising PBSC; ii) administering to the subject an agent which provides in vivo T cell depletion; iii) optionally expanding a population of γδ T cells ex vivo; and iv) administering to the subject a second graft infusion comprising T cells enriched in γδ T cells and depleted in αβ T cells.

In another embodiment, the method of HSCT comprises: i) administering to a subject on day 0 a minimally manipulated haploidentical hematopoietic stem cell graft infusion comprising PBSC; ii) administering to the subject an agent which provides in vivo T cell depletion; iii) optionally expanding a population of γδ T cells ex vivo; and iv) administering to the subject a second graft infusion comprising T cells enriched in γδ T cells and depleted in αβ T cells.

In another embodiment, the method of HSCT comprises: i) administering to a subject on day 0 a haploidentical hematopoietic stem cell graft infusion comprising PBSC; ii) administering to the subject an agent which provides in vivo T cell depletion; iii) expanding a population of γδ T cells ex vivo; iv) administering to the subject a second graft infusion comprising the expanded population of γδ T cells, wherein the expanded population of γδ T cells is enriched in γδ T cells and depleted in αβ T cells.

In another embodiment, the method of HSCT comprises: i) administering to a subject on day 0 a minimally manipulated haploidentical hematopoietic stem cell graft infusion comprising PBSC; ii) administering to the subject an agent which provides in vivo T cell depletion; iii) expanding a population of γδ T cells ex vivo; iv) administering to the subject a second graft infusion comprising the expanded population of γδ T cells, wherein the expanded population of γδ T cells is enriched in γδ T cells and depleted in αβ T cells.

In another embodiment, the method of HSCT comprises: i) obtaining a pool of PBSC from a haploidentical donor; ii) splitting the pool of PBSC into a first portion of PBSC to provide a PBSC product and a second portion of PBSC that is manipulated to provide a γδ T cell product which is enriched in γδ T cells and depleted in αβ T cells; iii) administering to a subject on day 0 a hematopoietic stem cell graft infusion comprising the PBSC product; iv) administering to the subject an agent which provides in vivo T cell depletion; v) optionally expanding a population of γδ T cells ex vivo in the γδ T cell product and vi) administering to the subject a second graft infusion comprising the γδ T cell product.

In another embodiment, the method of HSCT comprises: i) obtaining a pool of PBSC from a haploidentical donor; ii) splitting the pool of PBSC into a first portion of PBSC which is minimally manipulated to provide a PBSC product and a second portion of PBSC that is manipulated to provide a γδ T cell product which is enriched in γδ T cells and depleted in αβ T cells; iii) administering to a subject on day 0 a hematopoietic stem cell graft infusion comprising the PBSC product; iv) administering to the subject an agent which provides in vivo T cell depletion; v) optionally expanding a population of γδ T cells ex vivo in the γδ T cell product and vi) administering to the subject a second graft infusion comprising the γδ T cell product.

In another embodiment, the method of HSCT comprises: i) obtaining a pool of PBSC from a haploidentical donor; ii) splitting the pool of PBSC into a first portion of PBSC to provide a PBSC product and a second portion of PBSC that is manipulated to provide a γδ T cell product which is enriched in γδ T cells and depleted in αβ T cells; iii) administering to a subject on day 0 a hematopoietic stem cell graft infusion comprising the PBSC product; iv) administering to the subject an agent which provides in vivo T cell depletion; v) expanding a population of γδ T cells ex vivo in the γδ T cell product and vi) administering to the subject a second graft infusion comprising the γδ T cell product.

In another embodiment, the method of HSCT comprises: i) obtaining a pool of PBSC from a haploidentical donor; ii) splitting the pool of PBSC into a first portion of PBSC which is minimally manipulated to provide a PBSC product and a second portion of PBSC that is manipulated to provide a γδ T cell product which is enriched in γδ T cells and depleted in αβ T cells; iii) administering to a subject on day 0 a hematopoietic stem cell graft infusion comprising the PBSC product; iv) administering to the subject an agent which provides in vivo T cell depletion; v) expanding a population of γδ T cells ex vivo in the γδ T cell product and vi) administering to the subject a second graft infusion comprising the γδ T cell product.

In one embodiment of any of the foregoing, the method comprises administering to a subject a haploidentical PBSC infusion on day 0 followed by a γδ T cell infusion at +7 to plus +25 days.

In one embodiment of any of the foregoing, the method further comprises administering a preparative chemotherapy regimen prior to day 0.

In one embodiment of any of the foregoing, the method further comprises administering a T-cell depletion protocol after day 0.

In one embodiment of any of the foregoing, the method further comprises administering a GvHD prophylaxis regimen after day 0.

In one embodiment of any of the foregoing, the method further comprises administering a growth factor after day 0.

In one embodiment of any of the foregoing, the method further comprises a combination of at least two of: (i) administering a preparative chemotherapy regimen prior to day 0; (ii) administering a T-cell depletion protocol after day 0; (iii) administering a GvHD prophylaxis regimen after day 0; and (iv) administering a growth factor after day 0.

In one embodiment of any of the foregoing, the method further comprises a combination of at least three of: (i) administering a preparative chemotherapy regimen prior to day 0; (ii) administering a T-cell depletion protocol after day 0; (iii) administering a GvHD prophylaxis regimen after day 0; and (iv) administering a growth factor after day 0.

In one embodiment of any of the foregoing, the method further comprises a combination of each of: (i) administering a preparative chemotherapy regimen prior to day 0; (ii) administering a T-cell depletion protocol after day 0; (iii) administering a GvHD prophylaxis regimen after day 0; and (iv) administering a growth factor after day 0.

In one embodiment of any of the foregoing, the described method of HSCT will maximize a beneficial effect of infused donor T-cells (including, but not limited to, engraftment, immune reconstitution, and GvT). In another embodiment of any of the foregoing, the described method of HSCT will minimize a harmful effect of infused donor T-cells (such as, but not limited to, GvHD). In yet another embodiment of any of the foregoing, a combination of the foregoing is achieved by the method.

In one embodiment of any of the foregoing, PBSC grafts are collected from haploidentical donors and the cell product divided into an minimally manipulated HCT product that will be given on transplant day (as is standard in HSCT) and a γδ T cell product that will be given up to 25 days after the transplant, for example, in one embodiment, ≥3 days after. Using the methods of the present disclosure, boosting the γδ T cells (via infusion) after the post-transplant reduction of alloreactive T-cells that cause GvHD with a rapid immunosuppression taper will decrease the risk of relapse of hematological malignancy after haploidentical HCT.

In one embodiment of any of the foregoing, the number of PBSC infused in the haploidentical hematopoietic stem cell graft infusion is as known in the art. The selection of the number of cells to be infused may depend on a number of factors as is known in the art, such as but not limited to, the disease or condition to be treated and the condition of the subject.

In one embodiment of any of the foregoing, up to 5×10⁸ γδ T cells are infused in the second graft infusion. In one embodiment any of the foregoing, 1×10⁷ γδ T cells are infused in the second graft infusion. In one embodiment any of the foregoing, up to 5×10⁶γδ T cells are infused in the second graft infusion. In one embodiment of any of the foregoing, up to 5×10⁸ γδ T cells/kg are infused in the second graft infusion. In one embodiment any of the foregoing, 1×10⁷ γδ T cells/kg are infused in the second graft infusion. In one embodiment any of the foregoing, up to 5×10⁶γδ T cells/kg are infused in the second graft infusion. The selection of the number of cells to be infused may depend on a number of factors as is known in the art, such as but not limited to, the disease or condition to be treated and the condition of the subject.

In one embodiment, the second graft infusion or the γδ T cell product contains ≥60% γδ T cells. In one embodiment, the second graft infusion or the γδ T cell product contains ≥60% γδ T cells and ≤5% αβ T. In one embodiment, the second graft infusion or the γδ T cell product contains ≥60%γδ T cells, ≤5% αβ T cells and ≤25% NK cells.

In one embodiment of any of the foregoing, the methods of the present disclosure may be used in conjunction with any condition for which HSCT is used. In another embodiment of any of the foregoing, the condition is selected from one of the following: (i) patients with neoplastic hematological disorders with indication of allogeneic transplant according to the National Comprehensive Cancer Network (NCCN) or other standard guidelines as follows; (a) Acute lymphoblastic leukemia [ALL]²⁵ with high-risk features or relapsed disease (relapsed ALL); (b) Hodgkin²⁶ or Non-Hodgkin lymphoma²⁷ [HL or NHL]: relapsed disease where remission duration is less than 1 year, relapse after previous autologous transplant, or failure to achieve complete response (CR) with chemotherapy; and (c) Myeloid malignancy (such as for example acute myeloid leukemia [AML]²⁸ with intermediate/high-risk features (per NCCN criteria) or relapsed disease, OR chronic myeloid leukemia [CML]² in hematological remission or chronic phase).²ⁱ; (ii) myeloid disorder (such as for example myelodysplastic syndrome [MDS]³⁰ with intermediate/high risk features or refractory disease or myeloproliferative disorder; primary or secondary if high-risk features or refractory disease)³¹ and (iii) other conditions, such as, but not limited to, astrocytoma, ATRT (Atypical Teratoid Rhaboid Tumor), brain stem glioma, choroid plexus tumors, carcinoma and papilloma, craniopharyngioma, desmoplastic infantile astrocytoma, germ cell tumor, medulloblastoma, neurofibromatosis, oligodendroglioma, optic glioma, neuroblastoma, Ewing's Sarcoma, and PNET (Primitive Neuroectodermal Tumor).

In one embodiment of any of the foregoing, the methods of the present disclosure may be used in conjunction with a preparative chemotherapy regimen. In one embodiment, the preparative chemotherapy regimen is any known in the art. In another embodiment, the preparative chemotherapy regimen is one of the following (each of which is described in the methods section herein): (i) for myeloid diseases, the Fludarabine/Busulfan/total body irradiation preparative therapy may be used; (ii) for ALL or aggressive NHL or HL in patients </=40 years of age with no major comorbidities, the total body irradiation/cyclophosphamide (TBI/CY) preparative regimen may be used; or (iii) for ALL or lymphoma in patients who are older than 40 years, or at any age with major comorbidities that portends high non-relapse mortality (NRM) with high intensity Cy/TBI, the Fludarabine/TBI preparative regimen may be used.

In one embodiment of any of the foregoing, the methods of the present disclosure are used in combination with a in vivo T cell depletion protocol. In one embodiment, any such protocol known in the art may be used. In one embodiment, the T cell depletion protocol is cyclophosphamide treatment between days+1 and +10. In one embodiment, the T cell depletion protocol is cyclophosphamide treatment at between 30 and 70 mg/kg or 50 mg/kg. In one embodiment, the T cell depletion protocol is cyclophosphamide treatment at between 30 and 70 mg/kg or 50 mg/kg at days+3 and +4.

In one embodiment of any of the foregoing, a GvHD prophylaxis regimen is used. In one embodiment, the GvHD prophylaxis regimen is any known in the art. In another embodiment, the GvHD prophylaxis regimen provides for a decreased number of agents and/or a reduced concentration of one or more agents to be used, wherein the agent provides for suppression of the immune system. In another embodiment, the GvHD prophylaxis regimen is one of the following: (i) CELLCEPT® (mycophenolate mofetil) will be given as 15 mg/kg orally (PO) 3 times daily (maximum daily dose of 3 gm) starting day +5 to day +35. An intravenous formulation may be used as per physician discretion until reliable PO intake of the patient is established. Tacrolimus will be given as 0.03 mg/kg/day (dosing may be adjusted as is standard for drug interactions with concurrent medications) IV infusion beginning on day +5 and converted to oral tacrolimus when PO intake is tolerated. Tacrolimus will be continued until day +100 and then may be tapered to none by day +180 if there is no evidence of active GvHD; (ii) Tacrolimus will be given as 0.03 mg/kg/day (dosing may be adjusted as is standard for drug interactions with concurrent medications) IV infusion beginning on day +5 and converted to oral tacrolimus when PO intake is tolerated. Tacrolimus will be continued until day +100 and then may be tapered to none by day +180 if there is no evidence of active GvHD; or (iii) Tacrolimus will be given as 0.03 mg/kg/day (dosing may be adjusted as is standard for drug interactions with concurrent medications) IV infusion beginning on day +5 and converted to oral tacrolimus when PO intake is tolerated. Tacrolimus will be continued until day +50 and then may be tapered to none by day +100 if there is no evidence of active GvHD.

In one embodiment of any of the foregoing, the methods of the present disclosure may be used in conjunction with growth factor treatment. In one embodiment, any growth factor treatment regimen may be used. In another embodiment, the growth factor is granulocyte-colony stimulating factor (G-CSF). In another embodiment, G-CSF is administered from day +5 to about day +20 or from day +5 to about day +15. In another embodiment, the G-CSF is administered at about 5 mcg/kg on day +5 after transplant until neutrophil engraftment.

EXAMPLES

Example 1-αδ T Cell Depletion

Methods for αβ T cell depletion are known in the art and any method known in the art may be used. In one embodiment, the following method of αβ T cell depletion is used. The CLINIMACS® device with the α/β TCR Reagent Kit and other associated reagents is used for αβ T cell depletion. CLINIMACS® α/β TCR Reagent is a sterile monoclonal antibody reagent specific for αβ cells. The depletion of the αβ T-cells will be performed according to the manufacturer's instructions and as previously described (16). In brief, the leukapheresis/ex-vivo expanded product are incubated with the appropriate antibodies that are conjugated to magnetic particles and then are processed using the CLINIMACS® device (Miltenyi Biotec). CLINIMACS® plus Instrument is a software-controlled instrument that processes the blood sample (cell product). The CLINIMACS® Tubing Set is a single-use, sterile, disposable tubing set with proprietary cell selection columns. The CLINIMACS® PBS/EDTA Buffer is a sterile, isotonic, phosphate buffered, 1 mM EDTA saline solution is used as external wash and transport fluid for the in vitro preparation of blood cells.

Example 2—Ex-Vivo γδ T Cell Expansion

Methods for γδ T cell expansion are known in the art and any method known in the art may be used. In one embodiment, peripheral blood mononuclear cells (PBMC) are obtained via a peripheral blood draw or leukapheresis. The PBMC product is placed into culture at a density of 1-2× $10^6$/mL with addition of 2 mM ZOMETA® (Novartis, Inc.; zoledronic acid) and 100 u/mL Interleuken-2 (IL-2 Miltenyi Biotec, Bergish Gladbach, GERMANY) and appropriate GMP-grade base media culture or bioreactor system that allows monocytes to adhere (e.g. tissue culture plastic or the PRODIGY® bioreactor system (Miltenyi Biotech). Following 14 days of culture the cells are harvested and depleted of αβ T cells.

Preferably, the following method of αβ T cell depletion is used. The PRODIGY® OR CLINIMACS® device with the α/β TCR Reagent Kit and other associated reagents is used for αβ T cell depletion. CLINIMACS® α/β TCR Reagent is a sterile monoclonal antibody reagent specific for αβ cells. The depletion of the αβ T-cells is performed according to the manufacturer's instructions and as previously described (16). In brief, the leukapheresis/ex-vivo expanded product is incubated with the appropriate antibodies that are conjugated to magnetic particles and then is processed using the PRODIGY® or CLINIMACS® device (Miltenyi Biotec). CLINIMACS® plus Instrument is a software-controlled instrument that processes the blood sample (cell product). The PRODIGY® and CLINIMACS® Tubing Sets are single-use, sterile, disposable tubing sets with proprietary cell selection columns. The CLINIMACS® PBS/EDTA Buffer is a sterile, isotonic, phosphate buffered, 1 mM EDTA saline solution is used as external wash and transport fluid for the in vitro preparation of blood cells.

Example 3—Clinical Study

To be enrolled in the study, patients must fulfill all eligibility criteria and not be excluded by an exclusion criteria.

Eligibility Criteria

Eligibility criteria for the study are as follows:

(i) Patients with neoplastic hematological disorders with indication of allogeneic transplant according to the National Comprehensive Cancer Network (NCCN) or other standard guidelines as follows; (a) Acute lymphoblastic leukemia [ALL][25] with high-risk features or relapsed disease; (b) Hodgkin[26] or Non-Hodgkin lymphoma[27] [HL or NHL]: relapsed disease where remission duration is less than 1 year, relapse after previous autologous transplant, or failure to achieve CR with chemotherapy; and (c) Myeloid malignancy (acute myeloid leukemia [AML][28] with intermediate/high-risk features (per NCCN criteria) or relapsed disease, OR chronic myeloid leukemia [CML]29 in hematological remission or chronic phase)[28];

(ii) myeloid disorder (myelodysplastic syndrome [MDS][30] with intermediate/high risk features or refractory disease or myeloproliferative disorder; primary or secondary if high-risk features or refractory disease)[31];

(iii) No available suitable HLA-matched donor;

(iv) Age Criteria: 19 to 65 years in age;

(v) Organ Function Criteria: The following organ function testing should be done within 35 days before study registration: (a) Cardiac: LVEF of 50% or above, by MUGA or Echocardiogram; (b) Pulmonary: FVC, FEV1 and DLCO (corrected) should be 50% or above of expected; (c) Renal: serum creatinine level to be <2 mg/dl or estimated creatinine clearance (CrCl) must be equal or greater than 40 mL/min/1.73 m$^2$ as calculated by the Cockcroft-Gault Formula; and (d) Hepatic: serum bilirubin ≤1.5×upper limit of normal (ULN), Aspartate transaminase (AST)/alanine transaminase (ALT) ≤2.5×ULN, and alkaline phosphatase ≤2.5× ULN;

(vi) Performance status: Karnofsky ≥70%; and (vii) Consent: All patients must be informed of the investigational nature of this study and given written informed consent in accordance with institutional and federal guidelines.

Exclusion Criteria

The following exclusion criteria are applicable: (i) Non-compliant to medications; (ii) No appropriate caregivers identified; (iii) Uncontrolled medical or psychiatric disorders which may preclude patients to undergo clinical studies (Discretion of the attending physician); (iv) Active central nervous system (CNS) neoplastic involvement; (v) Patients with a known allergy to DMSO; (vi) HIV1 (Human Immunodeficiency Virus-1) or HIV2 positive; and (vii) Pregnant or breastfeeding.

The following donor eligibility criteria will also be followed: (i) HLA typing (A, B, C and DRB1 typed as high resolution); (ii) Suitable Donor—Medically cleared to donate; and (iii) Eligible Donor—Meets all donor screening and testing requirements related to transmission of infectious disease.

Study Treatment

Preparative Chemotherapy Regimens

The methods disclosed will be used to treat a variety of conditions. Depending on the condition to be treated, one of the following preparative regimens will be used.

For myeloid diseases, the Fludarabine/Busulfan/total body irradiation preparative therapy is used. This regimen is a modified Fludarabine plus Busulfan preparative regimen. When myeloablative Fludarabine plus Busulfan regimen is used, a total dose of busulfan that achieves an AUC (area under the concentration curve) of 20,000 is generally targeted. Since the protocols are adding post-transplant CY the busulfan target will be reduced to 16,000 AUC to minimize regimen related toxicity. Seizure prophylaxis will be administered per institutional guidelines while on busulfan. TBI of 400 cGy (given as 200 cGy ×2) will be given to achieve adequate immunosuppression to allow engraftment. Post-transplant CY of 50 mg/kg on Day +3 and +4 will also be given. Patients will receive MESNA (an organosulfur compound used as an adjuvant in cancer chemotherapy involving cyclophosphamide and ifosfamide for renal protection) and hydration for prophylaxis of hemorrhagic cystitis as per institutional guidelines. The regimen is further described below and illustrated in FIG. 1.

Day −7 Busulfan 60 mg IV (Test Dose with PK for AUC of 16,000)

Day −6 Fludarabine 40 mg/m$^2$ IV

Day −5 Busulfan PK directed dosing IV (with confirmatory PK), Fludarabine 40 mg/m$^2$ IV Day −4 Fludarabine 40 mg/m$^2$ IV Day −3 Busulfan PK directed dosing IV, Fludarabine 40 mg/m$^2$ IV Day −2 Busulfan PK directed dosing IV Day −1 Busulfan PK directed dosing IV (added this: different from the current protocol, I will change the graph below).

Day 0 TBI 200 cGy×2 fractions (Total dose 400 cGy) then transplant

Day +3 CY 50 mg/kg IV

Day +4 CY 50 mg/kg IV

Figure 2:
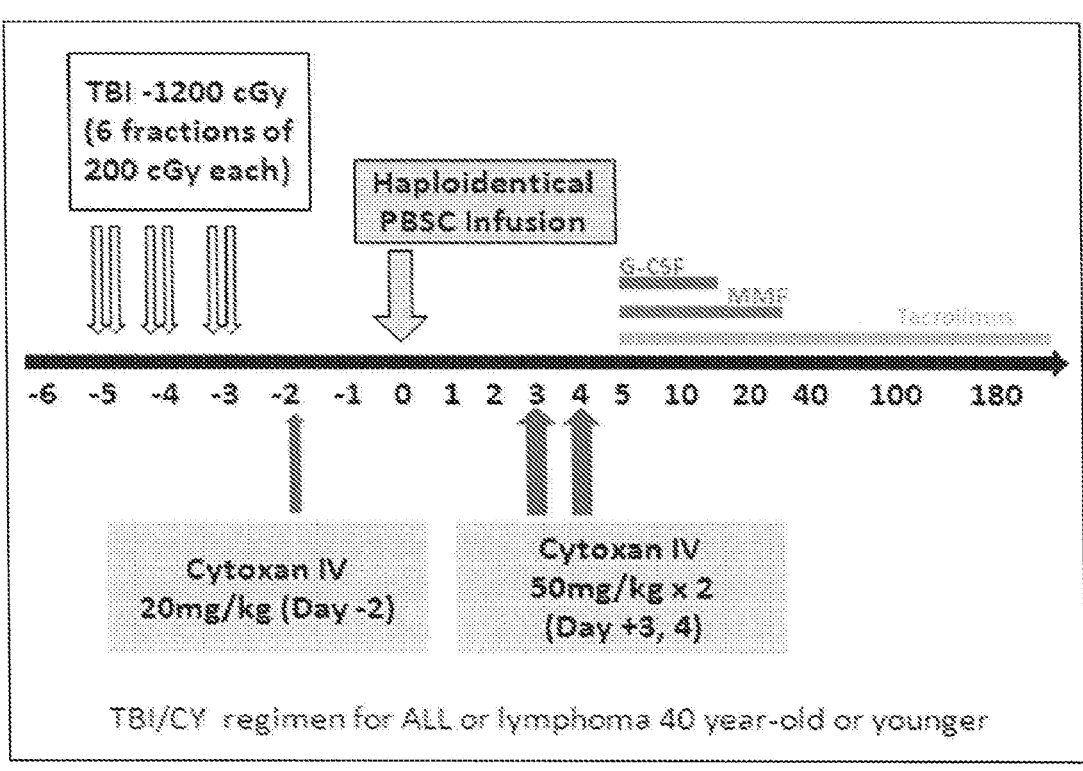
FIG. 2 Shows one embodiment of a preparative regimen ALL or Lymphoma patients 40 years old and younger using TBI/cyclophosphamide.

The total body irradiation/cyclophosphamide (TBI/CY) preparative regimen will be used for ALL or aggressive NHL or HL in patients <1=40 years of age with no major comorbidities. The standard myeloablative regimen for these patients is TBI 1,200 cGy and CY 60 mg/kg×2 days. In this study, the TBI dose will remain the same, but the pre-transplant CY dose will be decreased to 20 mg/kg on Day −2, and the post-transplant CY dose will be decreased to 50 mg/kg on Day +3 and +4. Thus, the total dose of CY is unchanged in this regimen. Patients will receive MESNA and hydration for prophylaxis of hemorrhagic cystitis as per institutional guidelines. The regimen is further described below and illustrated in FIG. 2.

Day −5 TBI 200 cGy/fraction (2 fractions)

Day −4 TBI 200 cGy/fraction (2 fractions)

Day −3 TBI 200 cGy/fraction (2 fractions)

Day −2 CY 20 mg/kg IV

Day −1 Rest

Day 0 Transplant

Day +3 CY 50 mg/kg IV

Day +4 CY 50 mg/kg IV

Figure 3:
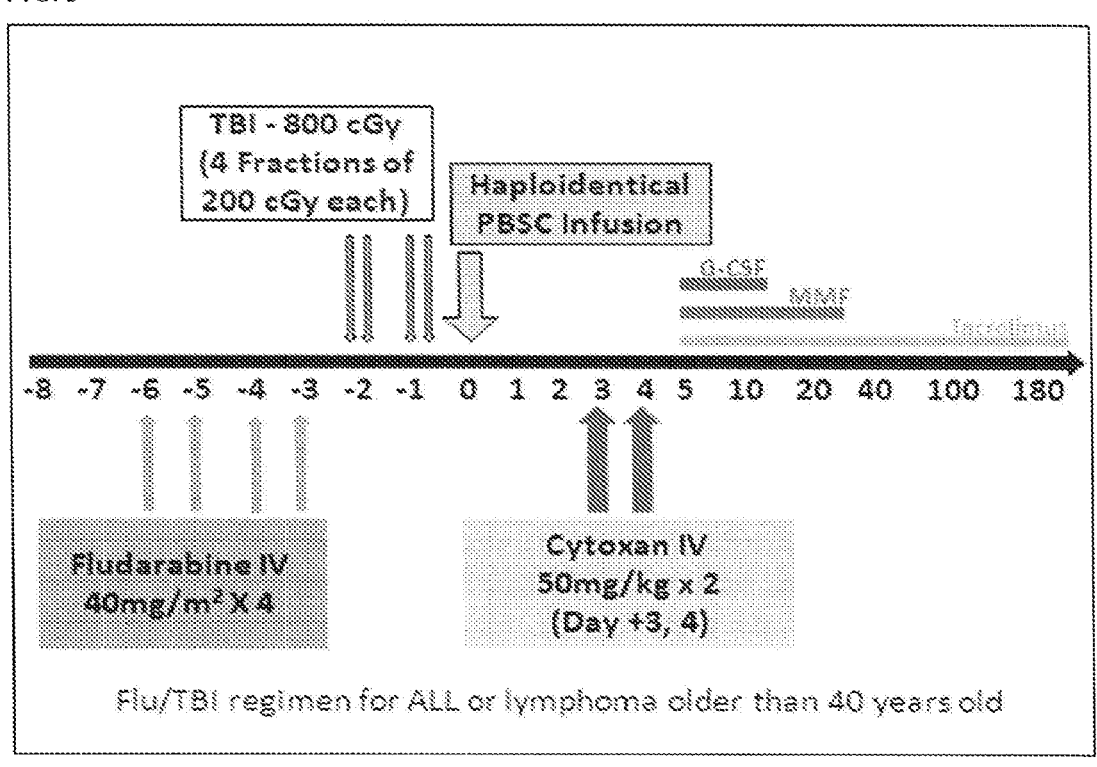
FIG. 3 Shows one embodiment of a preparative regimen for ALL or Lymphoma patients older than 40 years of age or at any age with major comorbidities.

The Fludarabine/TBI preparative regimen will be used for ALL or lymphoma in patients who are older than 40 years, or at any age with major comorbidities that portends high non-relapse mortality (NRM) with high intensity Cy/TBI. These patients will receive Fludarabine 40 mg/m$^2$×4 days plus TBI 800 cGy instead of the usual 1,200 cGy. Post-transplant CY of 50 mg/kg on Day +3 and +4 will be given. Patient will receive MESNA and hydration for prophylaxis of hemorrhagic cystitis as per institutional guidelines. The regimen is further described below and illustrated in FIG. 3.

Day −6 Fludarabine 40 mg/m$^2$ IV

Day −5 Fludarabine 40 mg/m$^2$ IV

Day −4 Fludarabine 40 mg/m$^2$ IV

Day −3 Fludarabine 40 mg/m$^2$ IV

Day −2 TBI 200 cGy/fraction (2 fractions)

Day −1 TBI 200 cGy/fraction (2 fractions)

Day 0 Transplant

Day +3 CY 50 mg/kg IV

Day +4 CY 50 mg/kg IV

Chemotherapy Dose Adjustment

Dosing of chemotherapy will be based on adjusted body weight unless the actual body weight is less than the ideal body weight (IBW), in which case we will use the actual body weight. Body weight is calculated as follows:

Ideal Body Weight (IBW):

Males: IBW=50+([(Ht. in cm×0.39)−60]×2.3)

Females: IBW=45.5+([(Ht. in cm×0.39)−60]×2.3)

Adjusted weight=IBW+(Actual Weight−IBW)×0.4

Donor Selection, Mobilization and Collection

For patients receiving an alpha/beta depleted donor leukocyte infusion, donors are screened for eligibility and suitability for allogeneic hematopoietic stem cell donation according to institutional procedures. The suitable and eligible haploidentical donor will undergo peripheral blood apheresis for the collection of stem cells on the day prior to transplant targeting a CD34+ cell dose of >5 ×10$^6$ cells/kg of recipient weight (more than 4×10$^6$ cells/kg). A portion of the product containing a minimum of 1×10$^5$ γδ T cells/kg will be removed for alpha/beta T cell depletion without reducing the transplant product below a CD34 dose of 4×10$^6$ CD34+ cells/kg. The manipulated fraction will be cryopreserved and stored until confirmation of neutrophil engraftment. If the total stem cell number collected is less than 5×10$^6$ cells/kg and/or the required γδ T cell dose cannot be obtained without reducing the CD34 dose below the 4×10$^6$ cells/kg, then the product will not be split for additional processing and the patient will be taken off of the study. If a participant is taken off of study before receiving the product, they will receive the post-transplant Cytoxan as per their assigned preparative regimen and continue to be followed for relapse.

For patients receiving ex vivo expanded/activated gamma/delta T cells, donors will be screened for eligibility and suitability for allogeneic hematopoietic stem cell donation according to institutional procedures. The suitable and eligible haploidentical donor will undergo peripheral blood apheresis for the collection of stem cells 8±1 days prior to transplant. This product will be designated for cell therapy product. Following this collection, the donor will be mobilized for a collection targeting a CD34+ cell dose of ≥4×10$^6$ cells/kg).

Cell Manufacturing

For γδ T cell expansion protocols, manufacturing will be performed in a standard biological safety cabinet in classified ISO 7 space under cGMP/cGMP manufacturing protocols. Donor apheresis product will be resuspended at 1.0-2.0×10$^6$/ml in commercial GMP grade T cell expansion medium with or without autologous serum, 2 μM Zoledronate (Novartis Oncology; East Hanover, NJ)+50 u/ml GMP grade IL-2 (Miltenyi Biotec) The culture is maintained at the original density for 14 days with addition of 50 u/ml IL-2 on post-culture days 2, 6, and 10 and addition of complete media as determined by pH and cell density. Composition, purity, and viability are determined by flow cytometry at day 0, +7 and +14 following initiation of culture. αβ T cells are depleted using the CLINIMACS®, PRODIGY® (Miltenyi Biotec, Auburn, CA) or other suitable bioreactor/cell separation system as described on Day +14±3. A final viability determination is obtained by flow cytometric analysis of To Pro Iodide incorporation or other cell viability stain. Our release criteria for the final product are ≥60% γδ T cells, ≤5% αβ T cells and ≤25% NK cells to be acceptable for infusion. Viability must be confirmed as ≥70% to release the product for infusion. Product with <70% viability will require exceptional release. Potency of the cell product is determined using in vitro cytotoxicity assays against K562 cells.

Stem Cell Infusion

Since a portion of the cell product to be given separately is cryopreserved, study participants will be exposed to dimethyl sulfoxide (DMSO) during the infusion of the minimally manipulated fraction. DMSO toxicity is a possible complication of cryopreserved product administration. Side effects and symptoms are generally associated with histamine release. Signs and symptoms include coughing, flushing, rash, chest tightness, wheezing, nausea, vomiting, and cardiovascular instability. Standard stem cell infusion precautions are taken to decrease the risk of reaction to the DMSO. These precautions include slowing the rate of infusion, pre-medicating with antihistamines, and continuous monitoring during administration.

Post-Transplant CY Treatment

Infusion of post-transplant CY (50 mg/kg) will take place on day +3 and day +4. MESNA will be administered as per institutional guidelines to prevent hemorrhagic cystitis.

γδ T Cell Infusion

The γδ T cell infusion will take place at any time from day +7 following transplant to day +3 following confirmation of neutrophil engraftment. This timing will permit infusion of the γδ T cell infusion after complete CY washout. The elimination half-life of CY is 3-12 hours (LexiComp monograph), thus the expected complete clearance after 5 half-lives (=60 hours) will occur before the anticipated infusion of the γδ T cell graft on day +7. Engraftment that is typically expected around day +14 to day +18. The product infusion will be performed as per the program's standard order set for the post-transplant infusion of donor cells. If the patient is in poor condition such as high fever, unstable blood pressure, or severe volume overload on day 7, infusion of the γδ T cell infusion may be withheld for 2 days (until day 9) at the attending physician's discretion. Also, if the patient develops renal insufficiency after post-transplant CY, infusion can be delayed until day 9 to ensure CY is cleared before γδ T cell infusion.

The infusion strategy will be as follows. Using a standard 3+3 Phase I escalation scheme, subjects will receive a fixed dose of $1\times10^7$ γδ T cells/kg. The first three subjects will receive a complete post-HSCT immunosuppression regimen as described above. The first patient of each group will undergo observation for 90 days prior to accruing the next patient into the protocol.

Prophylaxis

GvHD prophylaxis will consists of post-transplant CY (50 mg/kg IV on Day +3 and day +4 post-transplant). Other GvHD prophylaxis will include mycophenolate mofetil (MMF, CELLCEPT®) and a calcineurin inhibitor, such as tacrolimus, as needed. In one embodiment, the methods of the present disclosure allow for a reduced GvHD prophylaxis regimen.

In one embodiment, the GvHD regimen is as follows. CELLCEPT® will be given as 15 mg/kg PO 3 times daily (maximum daily dose of 3 gm) starting day +5 to day +35. An intravenous formulation may be used as per physician discretion until reliable PO intake of the patient is established. Tacrolimus will be given as 0.03 mg/kg/day (dosing may be adjusted as is standard for drug interactions with concurrent medications) IV infusion beginning on day +5 and converted to oral tacrolimus when PO intake is tolerated. Tacrolimus will be continued until day +100 and then may be tapered to none by day +180 if there is no evidence of active GvHD.

In another embodiment, the GvHD regimen is as follows. Tacrolimus will be given as 0.03 mg/kg/day (dosing may be adjusted as is standard for drug interactions with concurrent medications) IV infusion beginning on day +5 and converted to oral tacrolimus when PO intake is tolerated. Tacrolimus will be continued until day +100 and then may be tapered to none by day +180 if there is no evidence of active GvHD. In one aspect of this embodiment, the above regimen is utilized if no dose limiting toxicity is observed with the regimen in the preceding paragraph.

In yet another embodiment, the GvHD regimen is as follows. Tacrolimus will be given as 0.03 mg/kg/day (dosing may be adjusted as is standard for drug interactions with concurrent medications) IV infusion beginning on day +5 and converted to oral tacrolimus when PO intake is tolerated. Tacrolimus will be continued until day +50 and then may be tapered to none by day +100 if there is no evidence of active GvHD. In one aspect of this embodiment, the above regimen is utilized if no dose limiting toxicity is observed with the regimen in the preceding paragraph.

As such, using the methods of the present disclosure, a GvHD prophylaxis method that utilizes a minimum of agents and/or concentrations may be beneficially identified and used in combination with the methods of the present disclosure.

Infection prophylaxis will be carried out with anti-fungal, anti-bacterial, PCP, and anti-viral therapies as per institutional guidelines. Cytomegalovirus preemptive therapy will be followed with weekly CMV antigen screens or PCR monitoring starting approximately day +20 and continuing until the patient is off of immunosuppression. HHV6, EBV, and adenovirus PCR will be monitored at a minimum of every other week starting at approximately day +20 and continuing until the patient is off of immunosuppression.

A scheme for dose escalation is provided below

| Cohort | n | n experiencing Dose Limiting Toxicity (DLT) | Action |
|---|---|---|---|
| −1 (only enrolled if cohort exceeds Maximum Tolerated Dose (MTD)) γδ T cells: 5 × 10⁶ cells/kg | 3 | 0 or 1<br>2 | Continue accrual<br>Maximum dose exceeded. Close trial and reevaluate strategy |

-continued

| Cohort | n | n experiencing Dose Limiting Toxicity (DLT) | Action |
|---|---|---|---|
| MMF: 45 mg/kg/day +5 to day +35. Tacrolimus: 0.03 mg/kg/day IV day +5 to oral to day +180 with taper at +100 | | | |
| −1 | 6 | 1 or 2 | Expand to a total of 10 |
| | | 3 or more | subjects in Cohort −1 (only accrues if cohort 1 exceeds MTD) Maximum dose exceeded; Close trial and reevaluate strategy |
| 1 (starting cohort) | 3 | 0 | Taper immunosuppression |
| γδ T cells: 1 × 10⁷ cells/kg | | 1 | to next cohort |
| MMF: 45 mg/kg/day +5 to day +35. | | 2 | Continue accrual |
| Tacrolimus: 0.03 mg/kg/day IV day +5 to oral to day +180 with taper at +100 | | | Maximum dose exceeded; Deescalate to cohort −1 |
| 1 | 6 | 1 or 2 | Advance to next cohort |
| | | 3 or more | Maximum dose exceeded; Deescalate to cohort −1 |
| 2 | 3 | 0 | Taper immunosuppression |
| γδ T cells: 1 × 10⁷ cells/kg | | 1 | to next cohort |
| Tacrolimus: 0.03 mg/kg/day IV day +5 | | 2 | Continue accrual |
| to oral to day +180 with taper at +100 | | | Maximum dose exceeded; MTD is dose for Cohort 1 and accrual to a total of 10 subjects in Cohort 1 |
| 2 | 6 | 1 or 2 | Advance to next cohort |
| | | 3 or more | Maximum dose exceeded; MTD is dose for Cohort 1 and accrual to a total of 10 subjects in Cohort 1 |
| 3 | 3 | 0 or 1 | Continue accrual |
| γδ T cells: 1 × 10⁷ cells/kg | | 2 | Maximum dose exceeded; |
| Tacrolimus: 0.03 mg/kg/day IV day +5 | | | MTD is dose for Cohort 2 |
| to oral to day +100 with | | | and accrual to a total of 10 |
| taper at +50 | | | subjects in Cohort 2 |
| 3 | 6 | 1 or 2 | Continue accrual to 10 |
| | | 3 or more | subjects Maximum dose exceeded; MTD is dose for Cohort 2 and accrual to a total of 10 subjects in Cohort 2 |

Growth Factor Use

As part of the standard of care haploidentical transplant patients will be started on G-CSF 5 mcg/kg on day +5 after transplant until neutrophil engraftment.

Observations

The following observations will be monitored.

Pre-Transplant required observations: (within 35 days prior to study registration/day of transplant final evaluation)

1. History and physical exam (includes Karnofsky Performance Status score).
2. CBC, BUN, Creatinine, AST, ALT, Total bilirubin.
3. Echocardiogram or MUGA
4. Pulmonary function testing: FVC, FEV1, DLCO (corrected for hemoglobin).
5. Unilateral bone marrow aspirate and biopsy (for acute leukemia patients), morphology, and cytogenetics.
6. CT scans or Whole Body CT/PET scans if appropriate for disease status assessment.
7. Lumbar puncture will be done in patients with ALL. Pre-transplant intrathecal treatment(s) may be administered at the discretion of the attending physician.

In addition to the required observations noted above, allogeneic transplant recipients are recommended to have the following as appropriate for pre-transplant work-up: infectious disease markers (Hep A, Hep B, Hep C, HTLV, HIV, RPR, West Nile Virus, VZV, CMV, HSV, *Toxoplasma* IgG, GM assay); pregnancy screening; renal and liver functions lab panels; review of mammogram in female patients greater than 40 years of age; review of colonoscopy, or other appropriate GI screening, in patients greater than 50 years of age; review of PSA levels in males greater than 50 years of age; review of dental status; and review and evaluation of non-malignancy related co-morbid conditions.

Post-transplant required observations and follow-up plans:

Disease Status—As indicated by disease type and site, appropriate testing will be used to assess for disease status after transplant.

For leukemia patients: Bone marrow aspirate and biopsy specimen will be collected for morphology examination and cytogenetics at day +30 (±7), day +100 (±14), day +180 (±21), and 1 year (±45 days) post-transplant for all patients who are clinically stable and who have not demonstrated disease progression by that time point. In addition, a unilateral marrow aspirate will be collected whenever a relapse is suspected.

For lymphoma patients with no known history of bone marrow involvement: CT scans or Whole Body CT/PET scans will be performed at day +100 (±14), day +180 (±21), and 1 year (±45 days) post-transplant for all patients who are clinically stable and who have not demonstrated disease progression by that time point.

For lymphoma patients with history of bone marrow involvement: CT scans or Whole Body CT/PET scans will be performed at day +100 (±14), day +180 (±21), and 1 year (±45 days) post-transplant if appropriate and/or bone marrow aspirate and biopsy specimens will be collected for morphology examination and cytogenetics at day +30 (±7), day +100 (±14), day +180 (±21), and 1 year (±45 days) for all patients who are clinically stable and who have not demonstrated disease progression by that time point.

For the purpose of this study, relapse is defined by either morphological or cytogenetic evidence of disease in leukemia, or radiologic evidence (including the recurrence of fluoro-deoxyglucose [FDG]-avid lesions on PET scan) of progressive lymphoma.

Immune Reconstitution studies will be performed as per BMT standard and/or as clinically indicated. The recommended timing of the labs is at Day +30 (±7), Day +60 (±7), Day +100 (±14), Day +180 (±21), and at 1 year (±45 days) post-transplant. This panel will include measurement of the percentage and absolute count of CD3+, CD4+, CD8+, CD56+, CD19+, Treg (CD4+/CD25+) effector/memory, and GD T-cells.

Chimerism studies will be performed as per BMT standard to evaluate for sustained engraftment. The recommended timing of the labs is at Day +30 (±7), Day +60 (±7), Day +100 (±14), Day +180 (±21), and 1 year (±45 days) post-transplant.

Patients will be seen in clinic at least once a week (±3 days) until day +100 post-transplant to have a physical exam to assess for acute GvHD (using consensus criteria[32]). Then they will be seen at least once a month (±14 days)until 1 year post-transplant to have a physical exam to assess for chronic GvHD, and signs and symptoms of relapse or progression. Adverse Event and Toxicity monitoring will be performed at each visit date.

The patient will have cardiac function evaluation (Echocardiogram or MUGA scan), Pulmonary Function Tests (FVC, FEV1, and DLCO) and endocrine function tests (Thyroid Function Tests including TSH and free T4, and Random cortisol level) at one year after transplant. PFTs will be repeated yearly thereafter.

The study period is from the beginning of conditioning to day 100 post-transplant. The patient will be followed at least for 2 years after transplant for survival and relapse. The post 1 year follow-up interval is determined as clinically necessary. The patient who relapses after transplant will be followed only for survival.

Chemotherapy Drugs

Cytarabine. Cytarabine (1-β-D-Arabinofuranosylcytosine) is an antineoplastic drug of formula $C_9H_{13}N_3O_5$ (M.W. 243.22) used as a sterile solution for intravenous, intrathecal or subcutaneous administration. Cytarabine injection in combination with other approved anti-cancer drugs is indicated for remission induction in acute non-lymphocytic leukemia of adults and pediatric patients. It has also been found useful in the treatment of acute non-lymphocytic leukemia, acute lymphoblastic leukemia, acute myeloid leukemia, and the blast phase of chronic myelocytic leukemia. Intrathecal administration of Cytarabine injection (preservative free preparations only) is indicated in the prophylaxis and treatment of meningeal leukemia. It exhibits cell phase specificity, primarily killing cells undergoing DNA synthesis (S-phase) and under certain conditions blocking the progression of cells from the G1 phase to the S-phase. Although the mechanism of action is not completely understood, it appears that Cytarabine acts through the inhibition of DNA polymerase.

Cyclophosphamide (Cytoxan. CY). Cyclophosphamide is a synthetic antineoplastic drug chemically recognized as 2-[bis(2-cholorethyl)amino]tetrahydro-2H-1,3,2-oxaza-phosphorine 2-oxide monohydrate. The molecular formula of CY is $C_7H_{15}Cl_2N_2O_2P\cdot H_2O$ with a molecular weight of 279.1. CY for parenteral use must be prepared by either adding 0.9% sodium chloride solution, if injected directly, or sterile water, if infused. Constituted in water, CY is hypotonic; hence, it should not be injected directly. Solutions of CY with sodium chloride solution may be injected intravenously, intramuscularly, intraperitoneally, or intrapleurally. Constituted cylophosphamide is physically and chemically stable for 24 hours at room temperature or six days refrigerated. Prepared solutions do not contain any microbial preservative; hence, sterility of the solutions should be monitored.

Fludarabine (FLUDARA®). Fludarabine phosphate (fludarabine) is an antimetabolite with the chemical name 9H-Purin-6-amine, 2-fluoro-9-(5-0-phosphono-0-D-arabino-furanosyl) (2-fluoro-ara-AMP). The molecular formula is $C_{10}H_{13}FN_5O_7P$ with a molecular weight of 365.2. IV fludarabine is prepared by adding sterile water to the white solid cake. Reconstituted in 2 mL of sterile water, the solid cake produces a solution with an approximate concentration of 25 mg/mL fludarabine phosphate. Follow the institutional guidelines for further preparation and administration procedures of fludarabine. Reconstituted IV fludarabine contains no antimicrobial preservative; hence, it should be utilized within 8 hours of reconstitution. DO NOT infuse concomitantly with another intravenous solution of unknown compatibility.

Busulfan (BUSULFEX®). Busulfan is a bifunctional alkylating agent known chemically as 1,4-butanediol, dimethanesulfonate with a molecular formula of $CH_3SO_2O(CH_2)_4OSO_2CH_3$ and a molecular weight of 246 g/mole. IV busulfan must be diluted prior to use with either NS or D5W. The diluent quantity should be 10 times the volume of BUSULFEX®, so that the final concentration of busulfan is approximately 0.5 mg/mL. Infusion pumps should be used to administer the diluted busulfan solution. DO NOT infuse concomitantly with another intravenous solution of unknown compatibility. Warning: Rapid infusion of IV busulfan has not been tested and is not recommended. Busulfan is prepared and administered according to institutional guidelines.

Tacrolimus (PROGRAF®). Tacrolimus is a macrolide immunosuppressant produced by Stretocyces Tsukubaensis. Tacrolimus has an empirical formulation of $C_{44}H_{69}NO_{12}$— $H_2O$ and a formula weight of 822.05. Tacrolimus appears as white crystals or crystalline powder. It is practically insoluble in water, freely soluble in ethanol, and very soluble in methanol and chloroform. Tacrolimus inhibits T-lymphocyte activation, although the exact mechanism of action is not known. Experimental evidence suggests that tacrolimus binds to an intracellular protein, FKBP-12. A complex of tacrolimus-FKBP-12, calcium, calmodulin, and calcineurin is then formed and the phosphatase activity of calcineurin inhibited. This effect may prevent the dephosphorylation and translocation of nuclear factor of activated T-cells (NF-AT), a nuclear component thought to initiate gene transcription for the formation of lymphokines (such as interleukin-2, gamma interferon). The net result is the inhibition of T-lymphocyte activation (i.e., immunosuppression). Tacrolimus (PROGRAF® injection) must be diluted with NS or D5W before use. Tacrolimus is administered as a continuous infusion. Oral preparation will be administered on empty stomach every 12 hours.

Mycophenolate Mofetil (MMF. CELLCEPT®). CELL-CEPT® (mycophenolate mofetil) is the 2-morpholinoethyl ester of mycophenolic acid (MPA), an immunosuppressive agent, inosine monophosphate dehydrogenase (IMPDH) inhibitor. The chemical name for mycophenolate mofetil (MMF) is 2-morpholinoethyl (E)-6-(1,3-dihydro-4-hy-droxy-6-methoxy-7-methyl-3-oxo-5-isobenzofuranyl)-4-methyl-4-hexenoate. It has an empirical formula of $C_{23}H_{31}NO_7$ and a molecular weight of 433.50. Mycophenolate mofetil is a white to off-white crystalline powder. It is slightly soluble in water (43 μg/mL at pH 7.4); the solubility increases in an acidic medium (4.27 mg/mL at pH 3.6). It is freely soluble in acetone, soluble in methanol, and sparingly soluble in ethanol. The apparent partition coefficient in 1-octanol/water (pH 7.4) buffer solution is 238. The pKa values for mycophenolate mofetil are 5.6 for the morpholino group and 8.5 for the phenolic group. Myco-phenolate mofetil hydrochloride has a solubility of 65.8 mg/mL in D5W. The pH of the reconstituted solution is 2.4 to 4.1. Oral dosage formulations (tablet, capsule, suspension) should be administered on an empty stomach to avoid variability in MPA absorption. The oral solution may be administered via a nasogastric tube (minimum 8 French, 1.7 mm interior diameter); oral suspension should not be mixed with other medications. Delayed release tablets should not be crushed, cut, or chewed. Intravenous solutions should be administered over at least 2 hours (either peripheral or central vein); do not administer intravenous solution by rapid or bolus injection.

Filgrastim (NEUPOGEN®). NEUPOGEN® is the trade-mark name for filgrastim, representing recombinant methio-nyl human granulocyte colony-stimulating factor (r-methHuG-CSF). NEUPOGEN® is a 175 amino acid protein produced by recombinant DNA technology utilizing *Escherichia coli* (*E. coli*). NEUPOGEN® has a molecular weight of 18,800 daltons and an amino acid sequence similar to that of natural human DNA except for the additional methionine at the N-terminal, necessary for expression in *E. coli*. NEUPOGEN® may be administered as an IV or a subcutaneous infusion. It is recommended that NEUPO-GEN® be administered at least 24 hours after bone marrow infusion, with dosage modifications determined by neutro-phil response. If necessary, NEUPOGEN® maybe diluted in 5% dextrose with the addition of Albumin(human) to pre-vent absorption to plastic materials. Dilution to final con-centration less than 5 mcg/mL is not recommended at any time. Do not dilute with saline as the product may precipi-tate. When using either vials or prefilled syringes, do not save unused drugs for later administration. Dispose of all unused portions.

Total Body Irradiation (TBI). TBI will be administered per standard of care procedure as implemented by radiation oncologists. TBI alone for post-pubescent patients with dose/fractionation not exceeding 2 Gy×6 is well within the tolerance of most normal organs for <5% risk of severe late toxicity (organ failure or major dysfunction) by 5 years. Notable exceptions are risks of cataract development, bone marrow suppression, and ovarian and testicular dysfunction. Also, there is a small risk of second malignancy. The most common acute effects include nausea, vomiting, diarrhea, and painful swelling of the parotid glands. When TBI is given in conjunction with other therapies in the transplant setting, there is additional risk of side effects including loss of appetite, dry mouth, difficult or painful swallowing, headache, stomatitis (sore throat/mouth), altered skin integ-rity, hair loss, swelling, increased risk for infection and/or bleeding, possible lung failure, dry cough, fatigue, anxiety, fever, possible liver failure, lung scarring, loss of vision, shortness of breath, sterility, heartburn, cystitis, sleep dis-turbances, altered gastrointestinal and genitourinary func-tion, neuropathy, fistulas, altered endocrine function, peri-carditis, and increased risk of a second cancer. Overall, the incidence of most major toxicity when radiation is given in conjunction with other therapy as outlined above is still low, rare, serious side effects are possible.

Example 4—Results of Clinical Study

The expected outcome for the ABD study is that the incidence of acute GvHD will be no different from hap-loidentical transplant patients that receive post-transplant Cyclophosphamide without the supplemental ABD graft. This outcome is also expected for the EAGD patients while in addition we anticipate a lower incidence of infectious complications in the early post-transplant period (100 days) and a decreased incidence of relapsed disease (1, 2, and 5 years).

REFERENCES

[1] Copelan EA: Hematopoietic stem-cell transplantation. The New England journal of medicine 2006, 354:1813-26.

[2] Lee S J, Klein J, Haagenson M, Baxter-Lowe L A, Confer D L, Eapen M, Fernandez-Vina M, Flomenberg N, Horowitz M, Hurley C K, Noreen H, Oudshoorn M, Petersdorf E, Setterholm M, Spellman S, Weisdorf D, Williams T M, Anasetti C: High-resolution donor-recipi-ent HLA matching contributes to the success of unrelated donor marrow transplantation. Blood 2007, 110:4576-83.

[3] Alshemmari S, Ameen R, Gaziev J: Haploidentical hematopoietic stem-cell transplantation in adults. Bone marrow research 2011, 2011:303487.

[4] Aversa F, Terenzi A, Tabilio A, Falzetti F, Carotti A, Ballanti S, Felicini R, Falcinelli F, Velardi A, Ruggeri L, Aloisi T, Saab J P, Santucci A, Perruccio K, Martelli M P, Mecucci C, Reisner Y, Martelli M F: Full haplotype-mismatched hematopoietic stem-cell transplantation: a phase II study in patients with acute leukemia at high risk of relapse. Journal of clinical oncology: official journal of the American Society of Clinical Oncology 2005, 23:3447-54.

[5] Gale R P, Horowitz M M: Graft-versus-leukemia in bone marrow transplantation. The Advisory Committee of the International Bone Marrow Transplant Registry. Bone marrow transplantation 1990, 6 Suppl 1:94-7.

[6] Horowitz M M, Gale R P, Sondel P M, Goldman J M, Kersey J, Kolb H J, Rimm A A, Ringden 0, Rozman C, Speck B, et al.: Graft-versus-leukemia reactions after bone marrow transplantation. Blood 1990, 75:555-62.

[7] Ferrara J L, Yanik G: Acute graft versus host disease: pathophysiology, risk factors, and prevention strategies. Clinical advances in hematology & oncology: H&O 2005, 3:415-9, 28.

[8] Oevermann L, Handgretinger R: New strategies for haploidentical transplantation. Pediatric research 2012, 71:418-26.

[9] Lamb L S, Jr., Lopez R D: gammadelta T cells: a new frontier for immunotherapy? Biology of blood and mar-row transplantation: journal of the American Society for Blood and Marrow Transplantation 2005, 11: 161-8.

[10] Moretta L, Locatelli F, Pende D, Marcenaro E, Mingari M C, Moretta A: Killer 1g-like receptor-mediated control of natural killer cell alloreactivity in haploidentical hematopoietic stem cell transplantation. Blood 2011, 117:764-71.

[11] Palmer J M, Rajasekaran K, Thakar M S, Malarkannan S: Clinical relevance of natural killer cells following hematopoictic stem cell transplantation. Journal of Cancer 2013, 4:25-35.

[12] Lamb L S, Jr., Henslee-Downey P J, Parrish R S, Godder K. Thompson J, Lee C, Gee A P: Increased frequency of TCR gamma delta+ T cells in disease-free survivors following T cell-depleted, partially mismatched, related donor bone marrow transplantation for leukemia. Journal of Hematotherapy 1996, 5:503-9.

[13] Lamb L S, Jr., Gee A P, Hazlett L J, Musk P, Parrish R S, O'Hanlon T P, Geier S S, Folk R S, Harris W O, McPherson K, Lee C, Henslee-Downey P J: Influence of T cell depletion method on circulating gammadelta T cell reconstitution and potential role in the graft-versus-leukemia effect. Cytotherapy 1999, 1:7-19.

[14] Godder K T, Henslee-Downey P J, Mehta J, Park B S, Chiang K Y, Abhyankar S, Lamb L S: Long term disease-free survival in acute leukemia patients recovering with increased gammadelta T cells after partially mismatched related donor bone marrow transplantation. Bone Marrow Transplant 2007, 3 9:7 51-7.

[15] Handgretinger R: New approaches to graft engineering for haploidentical bone marrow transplantation. Seminars in oncology 2012, 39:664-73.

[16] Smetak M, Kimmel B, Birkmann J, Schaefer-Eckart K, Einsele H, Wilhelm M, Kunzmann V: Clinicalscale single-step CD4(+) and CDS(+) cell depletion for donor innate lymphocyte infusion DILi). Bone marrow transplantation 2008, 41:643-50.

[17] Girardi M, Oppenheim D E, Steele C R, Lewis J M, Glusac E, Filler R, Hobby P, Sutton B, Tigelaar R E, Hayday A C: Regulation of cutaneous malignancy by gammadelta T cells. Science 2001, 294:605-9.

[18] Kaminski M J, Cruz P D, Jr., Bergstresser P R, Takashima A: Killing of skin-derived tumor cells by mouse dendritic epidermal T-cells. Cancer Research 1993, 53:4014-9.

[19] Groh V, Rhinehart R, Secrist H, Bauer S, Grabstein K H, Spies T: Broad tumor-associated expression and recognition by tumor-derived gamma delta T cells of MICA and MICB. Proceedings of the National Academy of Sciences of the United States of America 1999, 96:6879-84.

[20] Bauer S, Groh V, Wu J, Steinle A, Phillips J H, Lanier L L, Spies T: Activation of NK cells and T cells by NKG2D, a receptor for stress-inducible MICA [see comments]. Science 1999, 285:727-9.

[21] Groh V, Steinle A, Bauer S, Spies T: Recognition of stress-induced MHC molecules by intestinal epithelial gammadelta T cells. Science 1998, 279:1737-40.

[22] Boismenu R, Havran W L: An innate view of gamma delta T cells. Curr Opin Immunol 1997, 9:57-63.

[23] Blazar B R, Taylor P A, Bluestone J A, Vallera D A: Murine gamma/delta-expressing T cells affect alloengraftment via the recognition of nonclassical major histocompatibility complex class 1b antigens. Blood 1996, 87:4463-72.

[24] Drobyski W R, Majewski D: Donor gamma delta T lymphocytes promote allogeneic engraftment across the major histocompatibility barrier in mice. Blood 1997, 89:1100-9.

[25] Drobyski W R, Hessner M J, Klein J P, Kabler-Babbitt C, Vesole D H, Margolis D A, Keever-Taylor C A: T cell depletion plus salvage immunotherapy with donor leukocyte infusions as a strategy to treat chronic-phase chronic myelogenous leukemia patients undergoing HLA-identical sibling marrow transplantation.[erratum appears in Blood 2000 Feb. 15;95(4):1137]. Blood 1999, 94:434-41.

[26] Neipp M, Exner B G, Maru D, Haber M, Gammie J S, Pham S M, Ildstad S T: T-cell depletion of allogeneic bone marrow using anti-alphabetaTCR monoclonal antibody: prevention of graft-versus-host disease without affecting engraftment potential in rats. Exp Hematol 1999, 27:860-7.

[27] Kawanishi Y, Passweg J, Drobyski W R, Rawlings P. Cook-Craig A, Casper J, Pietryga D, Garbrecht F, Camitta B, Horowitz M, Juckett M, Margolis D, Flomenberg N, Keever-Taylor C A: Effect of T cell subset dose on outcome of T cell-depleted bone marrow transplantation. Bone Marrow Transplantation 1997, 19:1069-77.

[28] Henslee P J, Thompson J S, Romond E H, Doukas M A, Metcalfe M, Marshall M E, MacDonald J S: T cell depletion of HLA and haploidentical marrow reduces graft-versus-host disease but it may impair a graft-versus leukemia effect. Transplantation Proceedings 1987, 19:2701-6.

[29] Ellison C A, MacDonald G C, Rector E S, Gartner J G: Gamma delta T cells in the pathobiology of murine acute graft-versus-host disease. Evidence that gamma delta T cells mediate natural killer-like cytotoxicity in the host and that elimination of these cells from donors significantly reduces mortality. J Immunol 1995, 155:4189-98.

[30] Schilbach K E, Geiselhart A, Wessels J T, Niethammer D, Handgretinger R: Human gammadelta T lymphocytes exert natural and IL-2-induced cytotoxicity to neuroblastoma cells. J Immunother 2000,23:536-48.

[31] Lamb L S, Jr., Musk P, Ye Z, van Rhee F, Geier S S, Tong J J, King K M, Henslee-Downey P J: Human gammadelta(+) T lymphocytes have in vitro graft vs leukemia activity in the absence of an allogeneic response. Bone Marrow Transplant 2001, 27:601-6.

[32] Cela M E, Holladay M S, Rooney C M, Richardson S, Alexander B, Krance R A, Brenner M K, Heslop H E: Gamma delta T lymphocyte regeneration after T lymphocyte-depleted bone marrow transplantation from mismatched family members or matched unrelated donors. Bone Marrow Transplant 1996, 17:243-7.

[33] Yabe M, Yabe H, Hattori K, Hinohara T, Morimoto T, Kato S, Kusunoki A: Transition of T cell receptor gamma/delta expressing double negative (CD4-/CD8-) lymphocytes after allogeneic bone marrow transplantation. Bone Marrow Transplant 1994, 14:741-6.

[34] Viale M, Ferrini S, Bacigalupo A: TCR gamma/delta positive lymphocytes after allogeneic bone marrow transplantation. Bone Marrow Transplant 1992, 10:249-53.

[35] Tsuji S, Char D, Bucy R P, Simonsen M, Chen C H, Cooper M D: Gamma delta T cells are secondary participants in acute graft-versus-host reactions initiated by CD4+ alpha beta T cells. European Journal of Immunology 1996,26:420-7.

[36] Keever-Taylor C A, Bredeson C, Loberiza F R, Casper J T, Lawton C, Rizzo D, Burns W H, Margolis D A, Vesole D H, Horowitz M, Zhang M J, Juckett M, Drobyski W R: Analysis of risk factors for the development of GVHD after T cell-depleted allogeneic BMT: effect of HLA disparity, ABO incompatibility, and method of T cell depletion. Biology of Blood & Marrow Transplantation 2001, 7:620-30.

[37] Mehta J, Singhal S, Gee A P, Chiang K Y, Godder K, Rhee Fv F, DeRienzo S, O'Neal W, Lamb L, HensleeDowney P J: Bone marrow transplantation from partially HLA-mismatched family donors for acute leukemia: single-center experience of 201 patients. Bone Marrow Transplant 2004,33:389 96.

[38] Lamb L S HLMP, et al.: Influence of T cell depletion method on circulating gd+ T cell reconstitution and potential role in the graft-versus-leukemia effect. Cytotherapy 1999, 1:7-19.

[39] Eto M, Mayumi H, Tomita Y, Yoshikai Y, Nishimura Y, Maeda T, Ando T, Nomoto K: Specific destruction of host-reactive mature T cells of donor origin prevents graft-versus-host disease in cyclophosphamide-induced tolerant mice. Journal of immunology 1991, 146:1402-9.

[40] Strauss G, Osen W, Debatin K M: Induction of apoptosis and modulation of activation and effector function in T cells by immunosuppressive drugs. Clinical and experimental immunology 2002, 128:255-66.

[41] Luznik L, Engstrom L W, Iannone R, Fuchs E J: Posttransplantation cyclophosphamide facilitates engraftment of major histocompatibility complex-identical allogeneic marrow in mice conditioned with lowdose total body irradiation. Biology of blood and marrow transplantation: journal of the American Society for Blood and Marrow Transplantation 2002, 8:131-8.

[42] Luznik L, Jalla S, Engstrom L W, Iannone R, Fuchs E J: Durable engraftment of major histocompatibility complex-incompatible cells after nonmyeloablative conditioning with fludarabine, low-dose total body irradiation, and posttransplantation cyclophosphamide. Blood 2001, 98:3456-64.

[43] Mayumi H, Umesue M, Nomoto K: Cyclophosphamide-induced immunological tolerance: an overview. Immunobiology 1996, 195:129-39.

[44] Burroughs L M, O'Donnell P V, Sandmaier B M, Storer B E, Luznik L, Symons H J, Jones R J, Ambinder R F, Maris M B, Blume K G, Niederwieser D W, Bruno B, Maziarz R T, Pulsipher M A, Petersen F B, Storb R, Fuchs E J, Maloney D O: Comparison of outcomes of HLA-matched related, unrelated, or HLA-haploidentical related hematopoietic cell transplantation following nonmyeloablative conditioning for relapsed or refractory Hodgkin lymphoma. Biology of blood and marrow transplantation: journal of the American Society for Blood and Marrow Transplantation 2008, 14:1279-87.

[45] Luznik L, O'Donnell P V, Symons H J, Chen A R, Leffell M S, Zahurak M, Gooley T A, Piantadosi S, Kaup M, Ambinder R F, Huff C A, Matsui W, Bolanos-Meade J, Borrello I, Powell J D, Harrington E, Warnock S, Flowers M, Brodsky R A, Sandmaier B M, Storb R F, Jones R J, Fuchs F J: HLA-haploidentical bone marrow transplantation for hematologic malignancies using nonmyeloablative conditioning and high-dose, posttransplantation cyclophosphamide. Biology of blood and marrow transplantation: journal of the American Society for Blood and Marrow Transplantation 2008, 14:641-50.

[46] Bronstein C G, Fuchs E J, Carter S L, Karanes C, Costa L J, Wu J, Devine S M, Wingard J R, Aljitawi O S, Cutler C S, Jagasia M H, Ballen K K, Eapen M, O'Donnell P V, Blood, Marrow Transplant Clinical Trials N: Alternative donor transplantation after reduced intensity conditioning: results of parallel phase 2 trials using partially HLA-mismatched related bone marrow or unrelated double umbilical cord blood grafts. Blood 2011, 118:282-8.

[47] Alvamas J C, Brown P A, Aoun P, Ballen K K, Bellam N, Blum W, Boyer M W, Carraway H E, Coccia P F, Coutre S E, Cultrera J, Damon L E, DeAngelo D J, Douer D, Frangoul H, Frankfurt 0, Goorha S, Millenson M M, O'Brien S, Petersdorf S H, Rao A V, Terezakis S, Uy G, Wetzler M, Zelenetz A D, Naganuma M, Gregory K M, National Comprehensive Cancer N: Acute lymphoblastic leukemia. Journal of the National Comprehensive Cancer Network: JNCCN 2012, 10:858-914.

[48] Hoppe R T, Advani R H, Ai W Z, Ambinder R F, Bello C M, Bierman P J, Blum K A, Dabaja B, Duron Y, Forero A, Gordon L I, Hemandez-Ilizaliturri F J, Hochberg E P, Maloney D G, Mansur D, Mauch P M, Metzger M, Moore J O, Morgan D, Moskowitz C H, Poppe M, Pro B, Weiss L, Winter J N, Yahalom J, Lymphoma N H: Hodgkin lymphoma. Journal of the National Comprehensive Cancer Network: JNCCN 2011, 9:1020-58.

[49] Zelenetz A D, Wierda W G, Abramson J S, Advani R H, Andreadis C B, Bartlett N, Bellam N, Byrd J C, Czuczman M S, Fayad L E, Glenn M J, Gockerman J P, Gordon L I, Harris N L, Hoppe R T, Horwitz S M, Kelsey C R, Kim Y H, Krivacic S, LaCasce A S, Nademanee A, Porcu P, Press 0, Pro B, Reddy N, Sokol L, Swinnen L, Tsien C, Vose J M, Yahalom J, Zafar N, Dwyer M A, Naganuma M, National Comprehensive Cancer N: NonHodgkin's lymphomas, version 1.2013. Journal of the National Comprehensive Cancer Network: JNCCN 2013, 11:257-72; quiz 73.

[50] O'Donnell M R, Tallman M S, Abboud C N, Altman J K, Appelbaum F R, Arber D A, Attar E, Borate U, Coutre S E, Damon L E, Lancet J, Maness L J, Marcucci G, Martin M G, Millenson M M, Moore J O, Ravandi F, Shami P J, Smith B D, Stone R M, Strickland S A, Wang E S, Gregory K M, Naganuma M: Acute myeloid leukemia, version 2.2013. Journal of the National Comprehensive Cancer Network: JNCCN 2013, 11:1047-55.

[51] O'Brien S, Radich J P, Abboud C N, Akhtari M, Altman J K, Berman E, DeAngelo D J, Deininger M, Devine S, Fathi A T, Gotlib J, Jagasia M, Kropf P, Moore J O, PalleraA, Pinilla-Ibarz J, Reddy V V, Shah N P, Smith B D, Snyder D S, Wetzler M, Gregory K, Sundar H: Chronic Myelogenous Leukemia, Version 1.2014. Journal of the National Comprehensive Cancer Network: JNCCN 2013, 11:1327-40.

[52] Greenberg P L, Attar E, Bennett J M, Bloomfield C D, Borate U, De Castro C M, Deeg H J, Frankfurt O, Gaensler K, Garcia-Manero G, Gore S D, Head D, Komrokji R, Maness L J, Millenson M, O'Donnell M R, Shami P J, Stein B L, Stone R M, Thompson J E, Westervelt P, Wheeler B, Shead D A, Naganuma M: Myelodysplastic syndromes: clinical practice guidelines in oncology. Journal of the National Comprehensive Cancer Network: JNCCN 2013, 11:838-74.

[53] Tefferi A: Primary myelofibrosis: 2013 update on diagnosis, risk-stratification, and management. American journal of hematology 2013, 88:141-50.

What is claimed:

1. A method for allogeneic hematopoietic stem cell transplantation (HSCT) in a subject suffering from a hematologic malignancy comprising the steps of:

(a) administering to the subject on day 0 an allogeneic hematopoietic stem cell first graft infusion, wherein the allogenic hematopoietic stem cells are haploidentical and minimally manipulated;

(b) After day 0, administering to the subject an agent which provides in vivo T cell depletion, wherein the agent is cyclophosphamide; and (c) After administering the agent which provides in vivo T cell depletion, administering to the subject a γδ T cell product, wherein the γδ cell product comprises an expanded population of γδ T cells and is depleted in αβ T cells, and further wherein the γδ cell product comprises greater than or equal to 60% γδ T cells, less than or equal to 5% αβ T cells, and less than or equal to 25% NK cells as determined by flow cytometric analysis;

wherein the method further comprises administering a preparatory chemotherapy regimen prior to day 0, and wherein the method reduces the risk of relapse of the hematologic malignancy.

2. The method of claim 1, wherein the γδ T cell product is administered about +7 to about +25 days-relative to day 0.

3. The method of claim 1, further comprising administering a Graft vs. Host Disease (GvHD) prophylaxis treatment regimen after day 0.

4. The method of claim 3, wherein the GvHD prophylaxis regimen comprises administering to the subject an immunosuppressive agent selected from cyclophosphamide (CY), mycophenolate mofetil (MMF), tacrolimus, or any combination thereof.

5. The method of claim 1, further comprising administering a growth factor after day 0.

6. The method of claim 5, wherein the growth factor is granulocyte-colony stimulating factor (G-CSF), the administration of which is selected from day +5 relative to day 0 to about day +20 relative to day 0.

7. The method of claim 1, wherein the number of infused γδ T cells in the γδ cell product is less than about $5\times10^8$ γδ T cells/kg of the subject's weight.

8. The method of claim 1 wherein the agent that provides in vivo T cell depletion is administered to the subject on any one or more days between +1 and +10 days relative to day 0.

9. The method of claim 1 wherein the hematologic malignancy is selected from: acute lymphoblastic leukemia (ALL); Hodgkin lymphoma (HL); Non-Hodgkin lymphoma (NHL); acute myeloid leukemia (AML); chronic myeloid leukemia (CML); and myelodysplastic syndrome (MDS).

10. The method of claim 1, wherein the preparative chemotherapy regimen is selected from Fludarabine/Busulfan/total body irradiation for myeloid diseases; total body irradiation/cyclophosphamide (TBI/CY) for acute lymphoblastic leukemia (ALL) or aggressive Non-Hodgkin lymphoma (NHL) or Hodgkin lymphoma (HL) in patients <40 years of age with no major comorbidities; and Fludarabine/total body irradiation for ALL or lymphoma in patients who are older than 40 years, or at any age with major comorbidities that portends high non-relapse mortality (NRM) with high intensity TBI/CY.

11. The method of claim 1, wherein the γδ T cell product is prepared by a method comprising ex vivo expansion.

12. The method of claim 1, wherein the agent which provides in vivo T cell depletion is administered at day +3 or +4 relative to day 0.

13. The method of claim 1, wherein the first graft infusion comprises PBSCs.

14. The method of claim 7, wherein the number of infused γδ T cells in the cell product is about $1\times10^7$ γδ T cells/kg of the subject's weight.

15. The method of claim 7, wherein the number of infused γδ T cells in the cell product is about $5\times10^6$ γδ T cells/kg of the subject's weight.

16. The method of claim 9, wherein the hematologic malignancy is relapsed ALL, relapsed HL, relapsed NHL or refractory MDS.

* * * * *